US008747861B2

(12) United States Patent
Ben-Yedidia et al.

(10) Patent No.: US 8,747,861 B2
(45) Date of Patent: Jun. 10, 2014

(54) MULTIMERIC MULTIEPITOPE INFLUENZA VACCINES

(75) Inventors: Tamar Ben-Yedidia, Mazkeret Batya (IL); Yossi Singer, Hashmonaim (IL)

(73) Assignee: BiondVax Pharmaceuticals Ltd., Ness Ziona (IL)

( * ) Notice: Subject to any disclaimer, the term of this patent is extended or adjusted under 35 U.S.C. 154(b) by 1110 days.

(21) Appl. No.: 12/671,617

(22) PCT Filed: Aug. 3, 2008

(86) PCT No.: PCT/IL2008/001062
§ 371 (c)(1),
(2), (4) Date: Apr. 1, 2011

(87) PCT Pub. No.: WO2009/016639
PCT Pub. Date: Feb. 5, 2009

(65) Prior Publication Data
US 2011/0182974 A1 Jul. 28, 2011

Related U.S. Application Data

(60) Provisional application No. 60/953,498, filed on Aug. 2, 2007.

(51) Int. Cl.
*A61K 39/145* (2006.01)
*A61K 39/00* (2006.01)
*A61K 39/12* (2006.01)
*A61K 39/295* (2006.01)

(52) U.S. Cl.
USPC .................. 424/206.1; 424/192.1; 424/184.1; 424/194.1; 424/204.1

(58) Field of Classification Search
None
See application file for complete search history.

(56) References Cited

U.S. PATENT DOCUMENTS

| | | | |
|---|---|---|---|
| 4,436,727 A | 3/1984 | Ribi | 424/177 |
| 4,474,757 A | 10/1984 | Arnon | 424/88 |
| 4,539,205 A | 9/1985 | Goodman | 514/45 |
| 4,643,992 A | 2/1987 | Goodman | 514/45 |
| 4,767,842 A | 8/1988 | Stevens | 530/324 |
| 4,866,034 A | 9/1989 | Ribi | 514/2 |
| 4,987,237 A | 1/1991 | Myers | 549/222 |
| 5,011,828 A | 4/1991 | Goodman | 514/45 |
| 5,057,540 A | 10/1991 | Kensil | 514/25 |
| 5,093,318 A | 3/1992 | Goodman | 514/45 |
| 5,683,695 A | 11/1997 | Shen et al. | |
| 5,709,879 A | 1/1998 | Barchfeld | 424/450 |
| 5,750,110 A | 5/1998 | Prieels | 424/208.1 |
| 5,776,468 A | 7/1998 | Hauser | 424/226.1 |
| 5,977,081 A | 11/1999 | Marciani | 514/25 |
| 6,022,960 A * | 2/2000 | Potter et al. | 536/23.1 |
| 6,063,386 A | 5/2000 | Dale | 424/244.1 |
| 6,080,725 A | 6/2000 | Marciani | 514/26 |
| 6,086,901 A | 7/2000 | O'Hagan | 424/283.1 |
| 6,113,918 A | 9/2000 | Johnson | 424/278.1 |
| 6,130,082 A | 10/2000 | Majarian | 435/252.3 |
| 6,303,347 B1 | 10/2001 | Johnson | 435/101 |
| 6,355,257 B1 | 3/2002 | Johnson | 424/278.1 |
| 6,740,325 B1 | 5/2004 | Arnon | 424/206.1 |
| 6,828,416 B1 | 12/2004 | Lal | 530/300 |
| 6,843,781 B2 | 1/2005 | Alchas | 604/117 |
| 7,063,967 B2 | 6/2006 | Johnson | 435/101 |
| 7,147,862 B1 | 12/2006 | Prieels | 424/208.1 |
| 7,250,036 B2 | 7/2007 | Alchas | 604/117 |
| 7,260,958 B2 | 8/2007 | Huang | 62/506 |
| 7,323,182 B2 | 1/2008 | Garcon | 424/278.1 |
| 7,794,731 B2 * | 9/2010 | Mizel et al. | 424/234.1 |
| 2004/0077540 A1 | 4/2004 | Quay | 514/12 |
| 2004/0223976 A1 | 11/2004 | Bianchi et al. | |
| 2009/0104216 A1* | 4/2009 | Torres | 424/186.1 |
| 2009/0304730 A1* | 12/2009 | Arnon et al. | 424/186.1 |
| 2010/0047275 A1* | 2/2010 | Stoloff et al. | 424/206.1 |
| 2010/0158943 A1 | 6/2010 | Vajdy et al. | |
| 2010/0189741 A1 | 7/2010 | Ballou et al. | |

FOREIGN PATENT DOCUMENTS

| | | |
|---|---|---|
| EP | 0 399 843 | 7/1994 |
| EP | 0624198 A1 | 11/1994 |
| GB | 9807805.8 | 4/1998 |
| WO | WO93/14206 | 7/1993 |
| WO | WO 93/14206 | 7/1993 |
| WO | WO 93/20846 | 10/1993 |
| WO | WO 95/17210 | 6/1995 |
| WO | WO 96/02555 | 2/1996 |
| WO | WO 96/33739 | 10/1996 |
| WO | WO 97/30721 | 8/1997 |
| WO | WO99/07839 A2 | 2/1999 |
| WO | WO 99/12565 | 3/1999 |
| WO | WO 99/52549 | 10/1999 |
| WO | WO 99/56776 | 11/1999 |
| WO | WO 01/21189 | 3/2001 |
| WO | WO 01/24810 | 4/2001 |

(Continued)

OTHER PUBLICATIONS

Flechtner et al, High-Affinity Interactions between Peptides and Heat Shock Protein 70 Augment CD8+ T Lymphocyte Immune Responses, J Immunol 2006; 177:1017-1027.*
Ada, G. L. and Jones, P. D. (1986) The immune response to influenza infection. Current Topics in Microbiology and Immunology, 128:1-54.
Arnon, R. et al., (2001) Peptide-based synthetic recombinant vaccines with anti-viral efficacy. Biologicals. 29(3-4):237-242.
Ben-Yedidia, Tamar et al., (1999) Intranasal administration of peptide vaccine protects human/mouse radiation chimera from influenza infection. Int Immunol. 1999; 11(7):1043-1051.
Baker, Phillip J. (1988) Inactivation of suppressor T-cell activity by nontoxic monophosphoryl lipid A. Infection and Immunity, 56(5):1076-1083.

(Continued)

*Primary Examiner* — Maria Marvich
(74) *Attorney, Agent, or Firm* — Winston & Strawn LLP

(57) ABSTRACT

The present invention relates to multimeric multi-epitope peptide-based vaccines. In particular, the present invention relates to the use of multimeric multi-epitope peptide-based vaccines eliciting protective immunity to influenza.

13 Claims, 10 Drawing Sheets

(56) References Cited

FOREIGN PATENT DOCUMENTS

Figure 4:
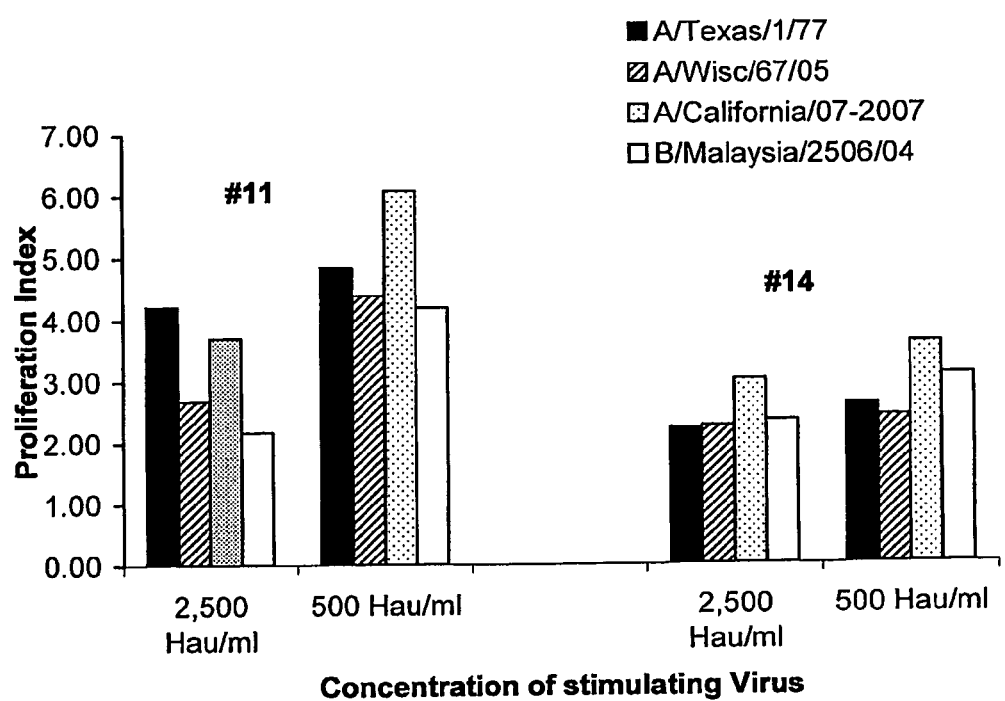

| WO | WO02/00885 A2 | 1/2002 |
| WO | WO2004/080403 A2 | 9/2004 |
| WO | WO 2006/069262 | 6/2006 |
| WO | WO 2006/078657 | 7/2006 |
| WO | WO 2006/128294 | 12/2006 |
| WO | WO 2007/066334 | 6/2007 |
| WO | WO2007/091030 A2 | 8/2007 |
| WO | WO 2008039267 * | 4/2008 |
| WO | WO 2009/026465 A2 | 2/2009 |

OTHER PUBLICATIONS

Caro-Aguilar, Ivette et al., (2005) Chimeric epitopes delivered by polymeric synthetic linear peptides induce protective immunity to malaria. Microbes and Infection 7(13):1324-1337.

Fournillier, A. et al., (2006) Primary and memory T cell responses induced by hepatitis C virus multiepitope long peptides. Vaccine 24(16):3153-3164.

Jegerlehner, Andrea et al., (2002) Regulation of IgG antibody responses by epitope density and CD21-mediated costimulation. Eur J Immunol. 32(11):3305-3314.

Lamb, Robert A. et al., (1985) Influenza virus M2 protein is an integral membrane protein expressed on the infected-cell surface. Cell. 40(3):627-633.

Liu, Wanli et al., (2004) High epitope density in a single recombinant protein molecule of the extracellular domain of influenza A virus M2 protein significantly enhances protective immunity. Vaccine 23(3):366-371.

Lopez, Jose Alejandro et al., (1993) Leishmania mexicana promastigotes induce cytotoxic T lymphocytes in vivo that do not recognize infected macrophages. Eur. J. Immunol. 23(1):217-223.

Otvos, Laszlo Jr., XP009112218, (2008) Synthesis of a multivalent, multiepitope vaccine construct. Methods in Molecular Biology 494:263-273.

Townsend, A. R. M. and Skehel, J. J. (1984) The influenza A virus nucleoprotein gene controls the induction of both subtype specific and cross-reactive cytotoxic T cells. J Exp Med 160(2):552-563.

Yang, Wen. et al., (2001) Multi-epitope schistosome vaccine candidates tested for protective immunogenicity in mice. Vaccine 19(1):103-113.

Ben-Yedidia, Tamar et al. ,XP000914823, (1998) Efficacy of anti-influenza peptide vaccine in aged mice. Mechanisms of Ageing and Development 104(1):11-23.

Ben-Yedidia and Arnon (2005) Review: Towards an epitope-based human vaccine for influenza. Hum Vaccin 1(3): 95-101.

Chen et al., (1999) Enhanced protection against A lethal influenza virus challenged by immunization with both hemagglutinin- and neuraminidase—expresseing DNAs. Vaccine 17(7-8): 653-659.

Horimoto et al., (2004) Influenza A viruses possessing type B hemagglutinin and neuraminidase: potential as vaccine components. Microbes Infect 6(6): 579-583.

Jeon et al., (2002) Intranasal immunization with synthetic recombinant vaccine containing multiple epitopes of influenza virus. Vaccine, 3214 (2002), 1-9.

Levi and Arnon (1996) Synthetic recombinant influenza vaccine induces efficient long-term immunity and cross-strain protection. Vaccine 14(1): 85-92.

Liu et al., (2005) Sequence comparison between the extracellular domain of M2 protein human and avian influenza A virus provides new information for bivalent influenza vaccine design. Microbes Infect 7(2): 171-177.

Shapira et al., (1985) A synthetic vaccine against influenza with built-in adjuvanticity. Int J Immunopharmacol 7(5): 719-723.

Slepushkin et al., (1995) Protection of mice against influenza A virus challenge by vaccination with baculovirus-expressed M2 protein. Vaccine 13(15): 1399-1402.

Zou et al., (2005) The epitope recognized by a monoclonal antibody in influenza A virus M2 protein is immunogenic and confers immune protection. Int Immunopharmacol 5(4): 631-635.

Li et al., (2003) Recombinant protein comprising multi-neutralizing epitopes induced high titer of antibodies against influenza A virus. Immunobiology 207(5): 305-13.

* cited by examiner

```
ATGCATATGAGATCTCCAGCTAAACTTCTGAAAGAACGTGGATTTTTCGGTGCAATCGCT
GGTTTTCTGGAGGGGTCGAAAGCCTACAGTAACTGTTACCCCTACGATGTGCCCGATTAT
GCCAGCCTGGGTAGCCTCCTTACAGAAGTTGAAACTTATGTGCTCGGCTGGCTGACAGGG
AAAAACGGCCTTTATCCTGTGTGGACCGGCGTGACGCAGAACGGATTCTGGCGTGGCGAA
AATGGACGTAAAACTCGCAGTGCGTATGAGCGCATGTGTAACATCCTCAAAGGTAAAGGC
CCGAAATATGTGAAACAGAATACATTAAAATTAGCCACCGGCGCGAGCGCTGCCTTTGAA
GACCTCCGTGTGCTCAGTTTTATCCGCGGTTATGGGGAACTGCGTTCTCGCTATTGGGCG
ATCCGTACCCGGTCAGGGGGTCCACCGGCGAAGCTGCTGAAAGAACGTGGGTTCTTCGGT
GCGATTGCCGGTTTCTTGGAAGGATCAAAAGCGTATTCGAACTGCTACCCGTATGATGTG
CCAGATTACGCCAGCCTGGGCTCCCTCTTGACAGAGGTCGAAACCTATGTACTGGGTTGG
CTGACCGGTAAGAACGGTCTGTATCCGGTTTGGACTGGTGTGACACAAAACGGCTTTTGG
CGGGGGGAAAACGGCCGGAAAACCCGCAGCGCTTACGAGCGCATGTGCAACATTCTGAAA
GGCAAAGGCCCGAAATACGTGAAGCAGAATACGCTCAAACTTGCCACGGGCGCAAGCGCA
GCCTTTGAAGACCTGCGGGTCTTGAGCTTTATCCGCGGTTACGGGGAGCTGCGGTCGCGC
TACTGGGCGATTCGTACGCGTAGTGGTGGACCTCCCGCGAAACTTCTGAAAGAGCGGGGC
TTCTTTGGAGCGATTGCGGGCTTCTTGGAGGGAAGCAAAGCCTACTCTAATTGTTACCCA
TACGATGTGCCTGATTATGCGAGCCTCGGTAGCTTGCTGACAGAAGTGGAAACCTACGTT
CTCGGCTGGCTGACGGGCAAAAATGGTCTCTACCCAGTGTGGACCGGAGTTACCCAGAAT
GGGTTCTGGCGCGGTGAGAACGGCCGTAAAACACGTTCAGCGTACGAGCGGATGTGCAAC
ATCTTAAAAGGCAAAGGACCGAAATACGTCAAGCAGAATACTCTGAAGTTAGCCACTGGG
GCCTCAGCCGCCTTTGAAGACCTTCGCGTCTTGAGTTTTATCCGGGGTTATGGGGAACTG
CGGAGCCGCTACTGGGCTATTCGTACGCGGTCGGGTGGCCCACTCGAGCCGGCCAAATTG
CTCAAAGAACGTGGTTTCTTCGGAGCGATCGCAGGTTTTCTTGAAGGCTCTAAAGCGTAC
AGCAACTGTTATCCATACGATGTGCCGGATTACGCCAGTCTGGGTTCCCTCCTGACCGAG
GTGGAAACGTATGTACTAGGATGGCTCACGGGTAAAAATGGTCTCTATCCTGTGTGGACG
GGCGTAACCCAGAACGGCTTTTGGCGGGGCGAAAACGGCCGCAAAACCCGTAGCGCATAC
GAGCGTATGTGTAACATCCTTAAAGGCAAAGGTCCAAAATACGTTAAGCAGAATACCCTG
AAACTGGCTACGGGCGCCAGTGCGGCCTTCGAAGATTTACGGGTGCTGTCCTTCATCCGC
GGCTATGGTGAACTGCGCTCTCGTTACTGGGCAATCCGTACCCGCAGTGGCGGACCTCCG
GCTAAACTGTTGAAAGAACGCGGCTTCTTTGGTGCTATCGCAGGTTTTCTGGAAGGAAGT
AAAGCATATTCGAATTGTTATCCCTACGACGTGCCGGATTATGCGTCGCTCGGTTCGCTG
CTGACCGAGGTGGAAACCTACGTTCTAGGCTGGTTGACAGGTAAGAACGGGCTTTACCCG
GTATGGACCGGCGTTACCCAGAACGGTTTTTGGCGCGGTGAAAATGGCCGTAAAACTCGG
TCAGCATACGAACGGATGTGCAATATCTTGAAAGGTAAAGGACCGAAATACGTTAAACAG
AACACGCTGAAACTGGCAACAGGCGCCAGCGCGGCGTTTGAGGATTTACGCGTCCTGTCA
TTTATTCGGGGCTACGGCGAATTACGTAGTCGTTATTGGGCGATTCGTACCCGCAGCGGA
GGGCTCGAGTAATAAAAGCTTTCTAGACATATGATGCAT
```

FIG. 1A

```
M H M R S P A K L L K E R G F F G A I A G F L E G S K A Y S
N C Y P Y D V P D Y A S L G S L L T E V E T Y V L G W L T G
K N G L Y P V W T G V T Q N G F W R G E N G R K T R S A Y E
R M C N I L K G K G P K Y V K Q N T L K L A T G A S A A F E
D L R V L S F I R G Y G E L R S R Y W A I R T R S G G P P A
K L L K E R G F F G A I A G F L E G S K A Y S N C Y P Y D V
P D Y A S L G S L L T E V E T Y V L G W L T G K N G L Y P V
W T G V T Q N G F W R G E N G R K T R S A Y E

```
ATGCATATGAGATCTCCAGCTAAACTTCTGAAAGAACGTGGATTTTTCGGTGCAATCGCT
GGTTTTCTGGAGCCACCGGCGAAGCTGCTGAAAGAACGTGGGTTCTTCGGTGCGATTGCC
GGTTTCTTGGAACCTCCCGCGAAACTTCTGAAAGAGCGGGGCTTCTTTGGAGCGATTGCG
GGCTTCTTGGAGCCATCGAAAGCCTACAGTAACTGTTACCCCTACGATGTGCCCGATTAT
GCCAGCCTGCCTTCAAAAGCGTATTCGAACTGCTACCCGTATGATGTGCCAGATTACGCC
AGCCTGCCAAGCAAAGCCTACTCTAATTGTTACCCATACGATGTGCCTGATTATGCGAGC
CTCCCTAGCCTCCTTACAGAAGTTGAAACTTATGTGCTCAGCTTGCTGACAGAAGTGGAA
ACCTACGTTCTCAGCTTGCTGACAGAAGTGGAAACCTACGTTCTCTGGCTGACAGGGAAA
AACGGCCTTTATCCTTGGCTGACCGGTAAGAACGGTCTGTATCCGTGGCTGACGGGCAAA
AATGGTCTCTACCCATGGACCGGCGTGACGCAGAACCCTTGGACTGGTGTGACACAAAAC
CCATGGACCGGAGTTACCCAGAATCCTTTCTGGCGTGGCGAAAATGGACGTAAAACTCGC
AGTGCGTATGAGCGCATGTGTAACATCCTCAAAGGTAAACCCTTTTGGCGGGGGGAAAAC
GGCCGGAAAACCCGCAGCGCTTACGAGCGCATGTGCAACATTCTGAAAGGCAAACCATTC
TGGCGCGGTGAGAACGGCCGTAAAACACGTTCAGCGTACGAGCGGATGTGCAACATCTTA
AAAGGCAAACCTCCGAAATACGTGAAGCAGAATACGCTCAAACTTGCCACGCCACCGAAA
TACGTCAAGCAGAATACTCTGAAGTTAGCCACTCCGCCGAAATACGTCAAGCAGAATACT
CTGAAGTTAGCCACTCCTTCAGCCGCCTTTGAAGACCTTCGCGTCTTGAGTTTTATCCGG
GGTTATCCAAGCGCAGCCTTTGAAGACCTGCGGGTCTTGAGCTTTATCCGCGGTTACCCT
TCAGCCGCCTTTGAAGACCTTCGCGTCTTGAGTTTTATCCGGGGTTATCCAGAACTGCGT
TCTCGCTATTGGGCGATCCGTACCCGGTCAGGGCCGGAGCTGCGGTCGCGCTACTGGGCG
ATTCGTACGCGTAGTGGTCCAGAACTGCGGAGCCGCTACTGGGCTATTCGTACGCGGTCG
GGTTAATAACTCGAGAGGCTTTCTAGACATATGATGCAT
```

*FIG. 2A*

```
M H M R S P A K L L K E R G F F G A I A G F L E P P A K L L
K E R G F F G A I A G F L E P P A K L L K E R G F F G A I A
G F L E P S K A Y S N C Y P Y D V P D Y A S L P S K A Y S N
C Y P Y D V P D Y A S L P S K A Y S N C Y P Y D V P D Y A S
L P S L L T E V E T Y V L S L L T E V E T Y V L S L L T E V
E T Y V L W L T G K N G L Y P W L T G K N G L Y P W L T G K
N G L Y P W T G V T Q N P W T G V T Q N P W T G V T Q N P F
W R G E N G R K T R S A Y E R M C N I L K G K P F W R G E N
G R K T R S A Y E R M C N I L K G K P F W R G E N G R K T R

```
ATGAGATCTCCGGCGAAACTGCTGAAAGAACGTGGCTTTTTTGGCGCGATTGCGGGCTTT
CTGGAAGGCAGCAAAGCGTATAGCAACTGCTATCCGTATGATGTGCCGGATTACGCGAGT
CTGGGCTCTCTGCTGACCGAAGTGGAAACCTATGTGCTGGGCTGGCTGACCGGCAAAAAC
GGCCTGTATCCGGTGTGGACCGGCGTGACCCAGAACGGCTTTTGGCGTGGCGAAAACGGC
CGTAAAACCCGTAGCGCGTATGAACGTATGTGCAACATCCTGAAAGGCAAAGGCCCGAAA
TATGTGAAACAGAACACCCTGAAACTGGCCACCGGTGCGAGCGCGGCGTTTGAGGACCTG
CGTGTTCTGAGCTTTATTCGTGGCTATGGCGAACTGCGTAGCCGTTATTGGGCGATTCGT
ACCCGTAGCGGTGGTCCGCCGGCCAAACTGCTGAAAGAACGCGGTTTCTTCGGTGCGATC
GCCGGTTTTCTGGAAGGTAGCAAAGCCTACTCTAATTGTTACCCGTACGATGTTCCGGAT
TACGCCAGCCTGGGTAGCCTGCTGACCGAAGTTGAAACCTACGTTCTGGGTTGGCTGACC
GGTAAAAATGGTCTGTACCCGGTTTGGACCGGTGTTACCCAGAATGGTTTCTGGCGCGGT
GAAAATGGTCGCAAAACCCGCAGCGCCTACGAACGCATGTGTAATATTCTGAAAGGTAAA
GGTCCGAAATACGTTAAACAGAATACCCTGAAACTGGCCACCGGCGCCAGCGCCGCCTTC
GAGGACCTGCGCGTTCTGAGCTTCATCCGCGGTTACGGTGAACTGCGCAGCCGCTACTGG
GCCATCCGCACCCGCAGCGGTGGTCCGCCGGCGAAACTGCTGAAAGAACGCGGTTTTTTT
GGTGCCATTGCGGGTTTTCTGGAAGGTAGCAAAGCCTATTCTAACTGCTATCCGTACGAT
GTTCCGGATTATGCGAGCCTGGGTAGCCTGCTGACCGAAGTGGAAACCTATGTTCTGGGT
TGGCTGACCGGCAAAAACGGTCTGTATCCGGTTTGGACCGGTGTGACCCAGAACGGTTTT
TGGCGCGGTGAAAACGGCCGTAAAACCCGCAGCGCCTATGAACGCATGTGCAACATTCTG
AAAGGCAAAGGTCCGAAATACGTGAAACAGAACACCCTGAAACTGGCCACCGGCGCGAGC
GCGGCCTTTGAGGACCTGCGCGTTCTGAGCTTTATTCGCGGCTATGGTGAACTGCGCAGC
CGCTATTGGGCGATTCGTACCCGCAGCGGCGGCTAATAACTCGAGAAGCTTTCTAGACAT
ATGATGCATGAGCTC
```

*FIG. 3A*

```
M R S P A K L L K E R G F F G A I A G F L E G S K A Y S N C
Y P Y D V P D Y A S L G S L L T E V E T Y V L G W L T G K N
G L Y P V W T G V T Q N G F W R G E N G R K T R S A Y E R M
C N I L K G K G P K Y V K Q N T L K L A T G A S A A F E D L
R V L S F I R G Y G E L R S R Y W A I R T R S G G P P A K L
L K E R G F F G A I A G F L E G S K A Y S N C Y P Y D V P D
Y A S L G S L L T E V E T Y V L G W L T G K N G L Y P V W T
G V T Q N G F W R G E N G R K T R S A Y E R M C N I L K G K
G P K Y V K Q N T L K L A T G A S A A F E D L R V L S F I R
G Y G E L R S R Y W A I R T R S G G P P A K L L K E R G F F
G

US 8,747,861 B2

MULTIMERIC MULTIEPITOPE INFLUENZA VACCINES

This application is a 371 filing of International Patent Application PCT/IL2008/001062 filed Aug. 3, 2008, which claims the benefit of application no. 60/953,498 filed Aug. 2, 2007.

FIELD OF THE INVENTION

The present invention relates to multimeric multi-epitope peptide-based vaccines. In particular, the present invention relates to the use of multimeric multi-epitope peptide-based vaccine eliciting protective immunity to influenza.

BACKGROUND OF THE INVENTION

Multi-Epitope Vaccines

It is known that B-cell epitopes, T-helper cell epitopes, and cytotoxic T lymphocytes epitopes all play important roles in these two immune responses. Obviously, broad spectrum and long lasting humoral and cellular responses should be induced for effective vaccination. There are still no broad spectrum and effective vaccines against viruses with high mutation rates, such as influenza virus and human immunodeficiency virus.

There is a close relationship between antigen dose and the efficiency of the specific B-cell response. Studies using a chemically coupled carrier protein and epitope peptide system, consisting of the same amount of carrier protein coupled with varying amounts of epitope peptide, have shown that epitope density dramatically affected T helper cell-dependent IgG responses (Jegerlehner et al., Eur J. Immunol. 2002, 32:3305-14). Liu et al. (Vaccine. 2004 23(3):366-71.) observed a positive effect of epitope density on the humoral response of mice and rabbits immunized with glutathione-S-transferase fusion proteins bearing various numbers of copies of the M2e peptide epitope (1, 2, 4, 8, and 16 copies) of the M2 protein of the influenza virus. In the same study, a lethal challenge assay showed that the fusion protein with the higher epitopes densities resulted in higher survival rates and slower weight losses.

Multi-epitope vaccines, namely vaccines comprising more than one epitope, have been developed for a wide variety of applications. A non-exhaustive list of examples includes, e.g., a recombinant multivalent vaccine for streptococcal bacteria disclosed in U.S. Pat. No. 6,063,386; a vaccine for treatment of malaria which comprises a single protein comprising peptides derived from different stages of the life cycle of the parasite *Plasmodium falciparum*, disclosed in U.S. Pat. No. 6,828,416; anti-tumor immunogenic compositions comprising a polypeptide comprising prostate stem cell antigen epitopes, disclosed in US Pat. Application 2007/0056315; and multi-epitope anti-viral vaccines against HIV (International Publication WO 01/24810), rubella virus (see International Publication WO 93/14206), and Hepatitis C virus (International Publication WO 01/21189).

International publication WO 2006/069262 discloses compositions, fusion proteins and polypeptides comprising Pathogen Associated Molecular Patterns (PAMP) and epitopes of influenza viral proteins used to stimulate immune responses in a subject. PAMPs are molecular motifs (e.g., proteins, peptides, nucleic acids, carbohydrates, lipids) found in microorganisms that can trigger an innate immune response in a host, i.e., act as adjuvant. In some embodiments the fusion proteins include multiple copies of the M2e influenza epitope. International publication WO 2006/078657 discloses similar fusion proteins and polypeptides comprising one or more PAMP and multiple epitopes of flaviviral proteins.

Influenza

Influenza is a disease caused by viruses of three main subtypes, Influenza A, B and C, which are classified according to their antigenic determinants. The influenza virion consists of a single stranded RNA genome closely associated with a nucleoprotein (NP) and enclosed by a lipoprotein envelope lined by matrix protein (M1) and carrying two major surface glycoprotein antigens, haemagglutinin (HA) and neuraminidase (NA). The HA and NA glycoproteins are most susceptible to change; for example, there are 16 immune classes of HA and 9 different NA classes that provide the basis for the different influenza virus subtypes like H1N1 or H3N2. Influenza A virus has an additional transmembrane glycoprotein, M2, which is highly conserved between the different HN subtypes. The M2 gene encodes a protein having 96-97-amino-acids that is expressed as a tetramer on the virion cell surface. It is composed of about 24 extracellular amino acids, about 19 transmembrane amino acids, and about 54 cytoplasmic residues (Lamb et al, Cell. 1985; 40:627-633.).

Influenza A and B viruses are the most common causes of influenza in man. Influenza has an enormous impact on public health with severe economic implications in addition to the devastating health problems, including morbidity and even mortality. Infection may be mild, moderate or severe, ranging from asymptomatic through mild upper respiratory infection and tracheobronchitis to a severe, occasionally lethal, viral pneumonia. Influenza viruses have two important immunological characteristics that present a challenge to vaccine preparation. The first concerns genetic changes that occur in the surface glycoproteins every few years, referred to as "antigenic drift". This antigenic change produces viruses that elude resistance elicited by existing vaccines. The second characteristic of great public health concern is that influenza viruses, in particular influenza A virus can exchange genetic material and merge. This process, known as "antigenic shift", results in new strains different from both parent viruses, which can be lethal pandemic strains.

Influenza Virus Antigens and Vaccine Production

Immunization towards influenza virus is limited by the antigenic variation of the virus and by the restriction of the infection to the respiratory mucous membranes. The influenza vaccines currently available are based either on whole inactive virus, on viral proteins presented on the surface of bacterial cells, or on flagellin bearing viral antigenic determinants. HA is a strong immunogen and is the most significant antigen in defining the serological specificity of the different virus strains.

The HA molecule (75-80 kD) comprises a plurality of antigenic determinants, several of which are in regions that undergo sequence changes in different strains (strain-specific determinants) and others in regions which are conserved in many HA molecules (common determinants). Due to these changes, flu vaccines need to be modified at least every few years.

Many influenza antigens, and vaccines prepared therefrom, are known in the art. U.S. Pat. No. 4,474,757 discloses a vaccine against influenza virus infections consisting of a synthetic peptide corresponding to an antigenic fragment of HA attached to a suitable macromolecular carrier, such as polymers of amino acids or tetanus toxoid.

PCT International Publication WO 93/20846 to some of the inventors of the present invention teaches a synthetic recombinant vaccine against a plurality of different influenza virus strains comprising at least one recombinant protein comprising the amino acid sequence of flagellin and at least one amino acid sequence of an epitope of influenza virus HA or NP, or an aggregate of said chimeric protein. Following this approach, a synthetic recombinant anti-influenza vaccine based on three epitopes was found to be highly efficient in mice. The exemplified vaccines included flagellin chimeras comprising the HA 91-108 epitope, a B-cell epitope from the HA which is conserved in all H3 strains and elicits anti-influenza neutralizing antibodies, together with one or both T-helper or CTL NP epitopes (NP 55-69 and NP 147-158, respectively), which induce MHC-restricted immune responses. A vaccine comprising a combination of the three above mentioned chimeras was considered to afford the best protection to viral infection.

U.S. Pat. No. 6,740,325 to some of the inventors of the present invention teaches a human synthetic peptide-based influenza vaccine comprising at least four epitopes of influenza virus, said influenza virus epitopes being reactive with human cells, said epitopes comprising:

(i) one B-cell haemagglutinin (HA) epitope; (ii) one T-helper haemagglutinin (HA) or nucleoprotein (NP) epitope that can bind to many HLA molecules; and (iii) at least two cytotoxic lymphocyte (CTL) nucleoprotein (NP) or matrix protein (M) epitopes that are restricted to the most prevalent HLA molecules in different human populations, in particular specific ethnic or racial groups. The influenza peptide epitopes can be expressed within recombinant *Salmonella* flagellin. That vaccine requires the cumbersome preparation of at least four chimeric polypeptides.

PCT International Publication WO 2007/066334 to some of the inventors of the present invention discloses a vaccine able to elicit long term and cross-strain protection comprising a plurality of chimeric proteins comprising at least two influenza virus peptide epitopes wherein at least one epitope is an influenza A virus matrix protein M peptide epitope and the second epitope is a hemagglutinin HA peptide epitope. In this case also the influenza peptide epitopes can be expressed within recombinant *Salmonella* flagellin.

Mammals often have acquired immune responses to flagellar antigens. However, clinical data have shown that effective doses of recombinant flagellin influenza in animals have adverse effects in human subjects, including high fever, probably due to the high flagellin/antigen ratio. It is also suspected that high concentrations of flagellin have a transient effect on the heart.

Thus there is an unmet need for an influenza peptide epitope-based vaccine which can induce humoral and cellular responses that are long-lasting with broad specificity. There is also a need for a vaccine with simplified production and quality control processes.

SUMMARY OF THE INVENTION

The present invention provides influenza vaccines that overcome the drawbacks of known vaccines against influenza, including the adverse effects of high carrier to antigen ratio and high adjuvant to antigen ratio. The vaccine of the present invention comprises polypeptide comprising multiple copies of plurality of influenza virus peptide epitopes, providing multi diversity, high density vaccine. According to the present invention the multimeric multiepitope polypeptide can be produced recombinantly, as an isolated polypeptide or as a fusion protein, or synthetically by linking a plurality of synthetic peptides, or can be mixed or formulated with an external adjuvant.

Multimeric polypeptides of the invention contain a combination of influenza virus B-cell epitopes, T-helper epitopes, and cytotoxic lymphocyte (CTL) epitopes. The epitopes are preferably selected from hemagglutinin (HA) peptides, matrix protein (M1 and M2) peptides, and nucleoprotein (NP) peptides. The epitopes have a demonstrable cross-protection activity against several human influenza subtypes and are chosen for their improved ability to induce a cellular and humoral immune response.

It was surprisingly found that several multimeric polypeptides according to the invention are active in eliciting an immune response even without being coupled to or without being part of a carrier protein. Furthermore, due to the high density and the variety of the immunogenic epitopes carried by the polypeptide, the vaccine elicits a strong immune response even without the need for an adjuvant. In addition, the inclusion of a large number of different immunogenic epitopes into a single polypeptide facilitates production procedures and quality control.

In a first aspect the present invention provides a synthetic or recombinant polypeptide comprising a plurality of influenza virus peptide epitopes each epitope is present at least twice in a single polypeptide. Within the context of this invention, a "multimeric" polypeptide is a polypeptide that contains a plurality of repeats (at least two, typically at least three or more), not necessarily adjacent, of an amino acid stretch of the polypeptide. The term "multimeric multiepitope" therefore relates to a polypeptide containing a plurality of repeats of a plurality of epitopes.

According to this aspect the present invention provides a synthetic or recombinant influenza multi-epitope polypeptide comprising multiple copies of a plurality of influenza virus peptide epitopes arranged in an alternating sequential polymeric structure $(X_1 X_2 X_3 \ldots)_n$ or in a block copolymer structure $(X_1)_n (X_2)_n (X_3)_n \ldots (X_m)_n$.

The synthetic or recombinant influenza multi-epitope polypeptide according to the present invention is selected from the group consisting of:

i. $B(X_1 Z X_2 Z \ldots X_m)_n B$; and
ii. $B(X_1)_n Z(X_2)_n Z \ldots (X_m)_n B$;

wherein B is an optional sequence of 1-4 amino acid residues; n is at each occurrence independently an integer of 2-50; m is an integer of 3-50; each of $X_1, X_2 \ldots X_m$ is an influenza peptide epitope consisting of 4-24 amino acid residues; Z at each occurrence is a bond or a spacer of 1-4 amino acid residues; and wherein the maximal number of amino acid residues in the polypeptide is about 1000.

According to some embodiments n is at each occurrence independently an integer of 2-50; m is an integer of 3-15; each of $X_1$-$X_m$ is an influenza peptide epitope selected from the group consisting of a B-cell type epitope, a T-helper (Th) type epitope, and a cytotoxic lymphocyte (CTL) type epitope, consisting of 4-24 amino acid residues; and the maximal number of amino acid residues in the polypeptide is about 600.

According to other embodiments the influenza peptide epitopes are selected from the group consisting of a hemagglutinin (HA) peptide, an M1 peptide, an M2 peptide, and a nucleoprotein (NP) peptide.

According to some specific embodiments, m is 4-9 and n is an integer of 3-6. Preferably, m is 9 and n is an integer of 3-5. According to other embodiments the influenza peptide epitopes are selected from the group consisting of SEQ ID NO:1 to SEQ ID NO:82.

According to some specific embodiments the influenza peptide epitopes are selected from epitopes E1-E9 according to table 1:

TABLE 1 influenza peptide epitopes E1 to E9

| Epitope | Epitope Type | Protein residues | Amino Acid Sequence | SEQ ID NO: |
|---|---|---|---|---|
| E1 | B cell | HA 354-372 | PAKLLKERGFFGAIAGFLE | 82 |
| E2 | B cell | HA 91-108 | SKAYSNCYPYDVPDYASL | 48 |
| E3 | B cell & CTL | M1 2-12 | SLLTEVETYVL | 25 |
| E4 | B cell | HA 150-159 | WLTGKNGLYP | 52 |
| E5 | B cell | HA 143-149 | WTGVTQN | 51 |
| E6 | T helper | NP 206-229 | FWRGENGRKTRSAYERMCNILKGK | 64 |
| E7 | T helper | HA 307-319 | PKYVKQNTLKLAT | 59 |
| E8 | CTL | NP 335-350 | SAAFEDLRVLSFIRGY | 69 |
| E9 | CTL | NP 380-393 | ELRSRYWAIRTRSG | 70 |

According to more specific embodiments the influenza peptide epitopes consist of: HA 354-372 (E1, SEQ ID NO: 82), HA 91-108 (E2, SEQ ID NO: 48), M1 2-12 (E3, SEQ ID NO: 25), HA 150-159 (E4, SEQ ID NO: 52), HA 143-149 (E5, SEQ ID NO: 51), NP 206-229 (E6, SEQ ID NO: 64), HA 307-319 (E7, SEQ ID NO: 59), NP 335-350 (E8, SEQ ID NO: 69), and NP 380-393 (E9, SEQ ID NO: 70).

According to yet other embodiments the polypeptide sequence is selected from the group consisting of: SEQ ID NO:84, SEQ ID NO:86, and SEQ ID NO:88.

According to some embodiments the polypeptide comprises nine different influenza virus peptide epitopes arranged in the following alternating sequential polymeric structure [E1E2E3E4E5E6E7E8E9]$_n$, wherein n is 3 or 5; E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

According to other embodiments the polypeptide comprises three repeats of nine different influenza virus peptide epitopes arranged in the following block copolymer structure [E1E1E1-E2E2E2-E3E3E3-E4E4E4-E5E5E5-E6E6E6-E7E7E7-E8E8E8-E9E9E9]$_n$, wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

According to yet other embodiments the polypeptide comprises six repeats of five different B-cell type influenza virus peptide epitopes arranged in the following alternating sequential polymeric structure [E1E2E3E4E5]$_6$, wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51).

According to other embodiments the polypeptide comprises six repeats of four different T-cell type influenza virus peptide epitopes arranged in the following alternating sequential polymeric structure [E7E8E9E6]$_6$, wherein E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

According to yet other embodiments the polypeptide comprises four repeats of four different T-cell type influenza virus peptide epitopes arranged in the following alternating sequential polymeric structure [E7E8E9E6]$_o$, where n is 6, and wherein E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70), and wherein said multimeric polypeptide is fused to a carrier protein.

According to additional embodiments the polypeptide comprises six repeats of nine different influenza virus peptide epitopes arranged in the following block copolymer structure [E2E2E2E2E2E2-E1E1E1E1E1E1-E3E3E3E3E3E3-E4E4E4E4E4E4-E5E5E5E5E5E5-E6E6EE6E6E66-E7E7E7E7'E7-E8E8E8E8E8E8-E9E9E9E9E9E9], wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

In various embodiments the polypeptide comprises at least two repeats of each epitope, typically at least three repeats of each epitope, alternatively at least four repeats, alternatively at least five repeats, alternatively at least six repeats of each epitope, maximum at least 50 repeats of each epitope. To improve the exposure of the epitopes to the immune system, the epitopes are preferably separated by a spacer, which according to certain embodiments consists of a single amino acid and according to other embodiments comprises at least one amino acid or is a peptide. Preferably, the spacer consists of 1-4 neutral amino acid residues.

According to specific embodiments the synthetic or recombinant influenza multi-epitope polypeptide consists of multiple copies of a plurality of influenza virus peptide epitopes arranged in an alternating sequential polymeric structure $(X_1X_2X_3\ldots)_n$ or in a block copolymer structure $(X_1)_n(X_2)_n(X_3)_n\ldots(X_m)_n$.

In some embodiments of this aspect of the present invention, the multimeric multiepitope polypeptide comprises at least two influenza peptide epitopes wherein at least one is selected from the group consisting of B-cell type epitopes, T-helper (Th) type epitopes, and cytotoxic lymphocyte (CTL) type epitopes. In some embodiments, the influenza peptide epitopes are selected from the group consisting of hemagglutinin (HA) peptide epitopes, matrix protein (M1 or M2) peptide epitopes, and nucleoprotein (NP) peptide epitopes. In certain preferred embodiments the peptide epitopes are selected from the group consisting of epitopes E1 to E9 according to Table 1.

Various exemplary embodiments are provided, comprising epitopes selected from Table 1, wherein the number of repeats for each epitope is the same or different, and wherein the polypeptide can be arranged in an alternating sequential polymeric structure or a block copolymer structure. The term "alternating sequential polymeric" structure means that a single copy of all the epitopes contained in the polypeptide are arranged sequentially and this arrangement is repeated sequentially a number of times equal to the number of repeats. For example, if the multimeric multiepitope polypeptide comprises four repeats of three epitopes $X_1$, $X_2$ and $X_3$ in an alternating sequential structure, the polypeptide has the following polymeric structure: $X_1X_2X_3$-$X_1X_2X_3$-$X_1X_2X_3$-$X_1X_2X_3$, also written $[X_1X_2X_3]_4$. The term "block copolymer" structure means that all the copies of a single epitope contained in the polypeptide are arranged adjacently. For example, a similar multimeric multiepitope polypeptide comprising four repeats of three epitopes $X_1$, $X_2$ and $X_3$ in a block copolymer structure has the following polymeric structure: $X_1X_1X_1X_1$-$X_2X_2X_2X_2$-$X_3X_3X_3X_3$, also written $[A]_4$-$[B]_4$-$[C]_4$.

According to some embodiments at least one amino acid of the spacer induces a specific conformation on a segment of the polypeptide (e.g. a proline residue).

According to yet other embodiments the spacer comprises a cleavable sequence. According to one embodiment the cleavable spacer is cleaved by intracellular enzymes. According to a more specific embodiment the cleavable spacer comprises a protease specific cleavable sequence.

According to some embodiments the multimeric polypeptide are preferably not conjugated to and are devoid of a carrier fusion protein. In other embodiments the polypeptides of the present invention may further comprise a carrier sequence, namely the peptide epitopes are inserted within a sequence of a carrier polypeptide or are coupled to a carrier sequence. According to some embodiments, the multimeric polypeptides are produced as a recombinant fusion protein comprising a carrier sequence.

In some specific embodiments the carrier sequence is a bacterial flagellin or a portion thereof. In certain embodiments, the multiepitope polypeptide is inserted within the hypervariable region of flagellin, thereby forming a recombinant flagellin fusion protein containing the multimeric multiepitope polypeptide. In other embodiments, the polypeptide is fused to an amino terminal or a carboxy terminal portion of the carrier protein.

The present invention provides, according to another aspect, isolated polynucleotide sequences encoding the influenza multi-epitope polypeptides.

According to some embodiments the isolated polynucleotide sequences encode a polypeptide sequence selected from the group consisting of: SEQ ID NO:84, SEQ ID NO:86, and SEQ ID NO:88.

According to specific embodiments, the isolated polynucleotide sequences comprise a sequence selected from the group consisting of: SEQ ID NO:83, SEQ ID NO:85, and SEQ ID NO:87.

According to yet another aspect, the present invention provides vaccine compositions for immunization of a subject against influenza comprising at least one synthetic or recombinant influenza multi-epitope polypeptide comprising multiple copies of a plurality of influenza virus peptide epitopes arranged in an alternating sequential polymeric structure $(X_1X_2X_3 \ldots)_n$ or in a block copolymer structure $(X_1)_n(X_2)_n(X_3)_n \ldots (X_m)_n$.

According to some embodiments the vaccine composition comprises at least two such polypeptides. According to some embodiments the vaccine comprises two polypeptides, wherein a first polypeptide comprises a plurality of B-cell type influenza virus peptide epitopes, and a second polypeptide comprises a plurality of T-cell type influenza virus peptide epitopes. According to a specific embodiment the first polypeptide is the polypeptide $[E1E2E3E4E5]_6$, wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51); and the second polypeptide is the polypeptide $[E7E8E9E6]_6$, wherein E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70), or a fusion carrier protein comprising the polypeptide $[E7E8E9E6]_n$, where n is 6, and wherein E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

Another aspect of the present invention provides a vaccine for immunization of a subject comprising a multimeric multiepitope polypeptide comprising a plurality of influenza virus peptide epitopes. In some embodiments the vaccine comprises at least three repeats of each epitope, alternatively at least four repeats, alternatively at least five repeats, alternatively at leak six repeats of each epitope. In some embodiments, the epitopes are separated by a spacer, which may be a single amino acid or a peptide of at least two amino acids.

In some embodiments, the vaccine comprises at least two influenza peptide epitopes wherein at least one epitope is selected from the group consisting of B-cell type epitopes, T-helper (Th) type epitopes, and CTL type epitopes. In some embodiments, the influenza peptide epitopes are selected from the group consisting of hemagglutinin (HA) peptide epitopes, M1 peptide epitopes, M2 peptide epitopes, and NP peptide epitopes. In preferred embodiments the peptide epitopes are selected from the group consisting of the epitopes E1 to E9 in Table 1 above.

In one embodiment the vaccine comprises three repeats of the nine epitopes E1-E9, arranged according to the alternating sequential polymeric structure $[E1E2E3E4E5E6E7E8E9]_3$. In another embodiment the vaccine comprises five repeats of the nine epitopes arranged according to the alternating sequential polymeric structure $[E1E2E3E4E5E6E7E8E9]_5$. In yet another embodiment the vaccine comprises three repeats of the nine epitopes arranged according to the block copolymer structure $[E1]_3$-$[E2]_3$-$[E3]_3$-$[E4]_3$-$[E5]_3$-$[E6]_3$-$[E7]_3$-$[E8]_3$-$[E9]_3$.

In yet another embodiment the vaccine comprises six repeats of the nine epitopes arranged according to the block copolymer structure $[E1]_6$-$[E2]_6$-$[E3]_6$-$[E4]_6$-$[E5]_6$-$[E6]_6$-$[E7]_6$-$[E8]_6$-$[E9]_6$.

Another aspect of the present invention provides a vaccine against influenza comprising a mixture of multimeric multiepitope polypeptides, wherein a first polypeptide comprises a plurality of B-cell type influenza virus peptide epitopes, and a second polypeptide comprises a plurality of T-cell type influenza virus peptide epitopes. Each of the multiepitope polypeptides may by part of a fusion protein with a carrier protein.

According to some embodiments the vaccine compositions according to the present invention do not contain an adjuvant. According to other embodiments the vaccine further comprises an adjuvant.

Pharmaceutically acceptable adjuvants include, but are not limited to water in oil emulsion, lipid emulsion, and liposomes. According to specific embodiments the adjuvant is selected from the group consisting of: Montanide®, alum, muramyl dipeptide, Gelvac®, chitin microparticles, chitosan, cholera toxin subunit B, Intralipid®, and Lipofundin®. According to a current preferred embodiment the adjuvant is Montanide®.

In some embodiments the vaccine is formulated for intramuscular, intranasal, oral, intraperitoneal, subcutaneous, topical, intradermal and transdermal delivery. In some embodiments the vaccine is administered intranasally. In other embodiments the vaccine is administered intramuscularly. In yet other embodiments the vaccine is administered intradermally.

The present invention provides according to a further embodiment a method for inducing an immune response and conferring protection against influenza in a subject, comprising administering to the subject a vaccine composition comprising at least one synthetic or recombinant influenza multiepitope polypeptide comprising multiple copies of a plurality of influenza virus peptide epitopes arranged in an alternating sequential polymeric structure $(X_1X_2X_3 \ldots)_n$ or in a block copolymer structure $(X_1)_n(X_2)_n(X_3)_n \ldots (X_m)_n$.

The route of administration of the vaccine is selected from intramuscular, intranasal, oral, intraperitoneal, subcutaneous, topical, intradermal, and transdermal delivery. According to preferred embodiments the vaccine is administered intranasally, intramuscularly or intradermally.

Use of a polypeptide according to the invention for preparation of a vaccine composition for immunization against influenza is also within the scope of the present invention, as well as use of an isolated polynucleotide according to the invention for production of a polynucleotide.

All the multimeric polypeptides disclosed in the present invention can be produced as a recombinant protein, a fusion protein, and by chemical synthesis. Accordingly, another aspect of the present invention provides a recombinant protein comprising a multimeric multiepitope polypeptide comprising a plurality of influenza virus peptide epitopes. In some embodiments the polypeptide is inserted within the hypervariable region of a bacterial flagellin.

Another aspect of the present invention provides a fusion protein comprising at least one multimeric multiepitope polypeptide and at least one additional polypeptide. In some embodiments the polypeptide is fused to a bacterial flagellin or a portion thereof. In a specific embodiment, the polypeptide comprising six repeats of the nine epitopes, arranged according to the block copolymer structure $[E1]_6$-$[E2]_6$-$[E3]_6$-$[E4]_6$-$[E5]_6$-$[E6]_6$-$[E7]_6$-$[E8]_6$-$[E9]_6$, is fused to a bacterial flagellin or a portion thereof.

Another aspect of the present invention provides a synthetic multimeric polypeptide comprising a plurality of synthetic peptide epitopes linked by a spacer selected from the group consisting of: a bond, an amino acid, and a peptide comprising at least two amino acids.

Encompassed by the present invention are also synthetic multimeric polypeptides for immunizing against influenza.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 1A and 1B show a multimeric polypeptide comprising five repeats of nine influenza peptide epitopes arranged in an alternating sequential polymeric structure: $(HA354-372---HA91-108---M1, 2-12---HA150-159---HA143-149---NP206-229---HA307-319---NP335-350---NP380-393)_5$. (A) the nucleotide sequence (SEQ ID NO:83) of the construct used to produce a multimeric polypeptide; (B) the amino acid sequence (SEQ ID NO:84) of the multimeric polypeptide encoded by the nucleotide sequence of A. The epitopes in the first sequence of nine epitopes are underlined.

FIGS. 2A and 2B show a multimeric polypeptide comprising three repeats of nine influenza peptide epitopes arranged in a block copolymer structure: $(HA354-372)_3$---$(HA91-108)_3$---$(M1\ 2-12)_3$---$(HA150-159)_3$---$(HA143-149)_3$---$(NP206-229)_3$---$(HA307-319)_3$---$(NP335-350)_3$---$(NP380-393)_3$. (A) Nucleotide sequence (SEQ ID NO:85) of the construct used to produce the polypeptide. (B) Amino acid sequence (SEQ ID NO:86) of the multimeric polypeptide. The three repeats of the first epitope are underlined.

FIGS. 3A and 3B show a multimeric polypeptide comprising three repeats of nine influenza peptide epitopes arranged in an alternating sequential polymeric structure: $(HA354-372---HA91-108---M1, 2-12---HA150-159---HA143-149---NP206-229---HA307-319---NP335-350---NP380-393)_3$. (A) Nucleotide sequence (SEQ ID NO:87) of the construct used to produce the polypeptide. (B) Amino acid sequence (SEQ ID NO:88) of the multimeric polypeptide. The epitopes in the first sequence of nine epitopes are underlined.

FIG. 4 shows the cellular immune response to several strains of influenza viruses, of mice vaccinated with two multimeric vaccines: #11 and #14. The cellular immune response to two different concentrations of a stimulating virus was measured and is shown as the proliferation index for lymphocytes incubated with a stimulating virus.

FIG. 5 shows the protective effect of multimeric vaccine #14 against a highly lethal dose of a mouse adapted influenza virus H3N2 strain (A/Texas/1/77). The protective effect of the vaccine is demonstrated by a significant reduction in virus titer in the lungs of vaccinated mice compared to control mice (PBS).

FIGS. 6A and 6B show the efficacy of several multimeric vaccines in protecting mice from a viral challenge. The protective effect of multimeric vaccine #11, #12 and #14 is demonstrated by a higher survival rate (FIG. 6A) of vaccinated mice compared to control (PBS) mice, following infection with a lethal dose of a mouse adapted influenza virus H3N2 strain (A/Texas/1/77), and by a significantly lower viral load in lungs (FIG. 6B) of vaccinated mice compared to control (50% Gly/PBS) mice.

FIG. 7 compares the efficacy of immunization of mice with several vaccines comprising multimeric constructs in 50% Glycerol in PBS (#11, #12, and #14) or in emulsion with Incomplete Freund's adjuvant (#11-IFA, #12-IFA, and #14-IFA). The protective effect of the different vaccines and the effect of the IFA are measured by the survival rate of vaccinated mice compared to control mice after challenge with the mouse adapted influenza virus H3N2 strain (A/Texas/1/77).

DETAILED DESCRIPTION OF THE INVENTION

The present invention provides multimeric multiepitope polypeptides and vaccines based on these polypeptides, comprising a plurality of influenza virus peptide epitopes. A polypeptide according to the present invention comprises at least two repeats of each epitope. Preferably a polypeptide according to the present invention comprises at least three repeats of each epitope. The present invention also provides vaccines based on such polypeptides and methods of use thereof.

Peptide epitopes derived from influenza proteins are useful in preparing vaccines against influenza. However, each peptide alone is almost invisible to the immune system, is degraded rapidly and arouses an insufficient immune response. When multiple copies of immunogenic peptides are presented to the immune system as single polypeptide, the magnitude of the epitope-specific immune response is enhanced. For example, vaccines based on a recombinant flagellin fusion protein containing a single copy of one influenza peptide epitope provide an epitope/flagellin ratio of approximately 1:28. By using multi-epitope vaccines, containing a plurality of epitopes in several copies each, a epitope/flagellin ratio of up to 2:1 can be obtained. The present invention discloses multimeric multiepitope polypeptides with enhanced immunogenicity compared to the known constructs and configurations. The polypeptides each contain a plurality of epitopes, wherein each epitope is repeated in multiple copies. The multiple copies or repeats of each epitope may be contiguous as a block of each epitope. Alternatively the plurality of epitopes may appear in a predetermined sequence where this sequence is repeated a number of times within the polypeptide. Both these types of configurations of the multiple epitopes are now shown to have unexpectedly superior results in conferring immunity against influenza on a subject.

Definitions

For convenience, certain terms employed in the specification, examples and claims are described herein.

The term "antigen presentation" means the expression of antigen on the surface of a cell in association with major histocompatibility complex class I or class II molecules (MHC-I or MHC-II) of animals or with the HLA-I and HLA-II of humans.

The term "immunogenicity" or "immunogenic" relates to the ability of a substance to stimulate or elicit an immune response. Immunogenicity is measured, for example, by determining the presence of antibodies specific for the substance. The presence of antibodies is detected by methods known in the art, for example using an ELISA assay.

Influenza epitopes can be classified as B-cell type, T-cell type or both B cell and T cell type, depending on the type of immune response they elicit. The definition of B cell or T cell peptide epitope is not unequivocal; for example, a peptide epitope can induce antibody production but at the same time that epitope can possess a sequence that enables binding to the human HLA molecule, rendering it accessible to CTLs, hence a dual B cell and T cell classification for that particular epitope. "CTL", "killer T cells" or "cytotoxic T cells" is a group of differentiated T cells that recognize and lyse target cells bearing a specific foreign antigen that function in defense against viral infection and cancer cells. "T helper cell" or "Th" is any of the T cells that when stimulated by a specific antigen release cytokines that promote the activation and function of B cells and killer T cells.

The term "recombinant flagellin fusion protein" refers to a flagellin polypeptide comprising a peptide epitope or a multimeric multiepitope polypeptide embedded within its sequence, or alternatively, to a portion of a flagellin polypeptide fused to a peptide epitope or a multimeric multiepitope polypeptide at either its N- or C-terminus.

"Amino acid sequence", as used herein, refers to an oligopeptide, peptide, polypeptide, or protein sequence, and fragment thereof, and to naturally occurring or synthetic molecules.

In the specification and in the claims the term "spacer" denotes any chemical compound, which may be present in the polypeptide sequence, at one of the terminals or between two epitopes. Preferably, the spacer consists of 1-4 amino acid residues. The spacer may comprise a sequence that can be cleaved by enzymatic means, or may decompose spontaneously. The spacer may enforce or induce beneficial conformation to the polypeptide. The spacer may optionally comprise a protease specific cleavable sequence.

Peptide Epitopes Useful in Preparing a Vaccine

According to preferred embodiments of the present invention, peptide epitopes are derived from influenza proteins selected from the group consisting of HA, M1, M2, and NP. The epitopes may also be selected according to their type: B-cell type, Th type, and CTL type.

It is to be noted that peptide epitopes listed herein are provided as for exemplary purposes only. The influenza virus proteins vary between isolates, thereby providing multiple variant sequences for each influenza protein. Accordingly, the present invention encompasses peptide epitopes having one or more amino acid substitutions, additions or deletions.

The matrix protein M1 is a major structural component of the influenza virus particles and forms an inner layer of the lipid cell-derived envelope. Within the virion and in infected cells at late stages of the virus replication, the M1 protein associates with the viral ribonucleoproteins (vRNPs), which are composed of viral RNA molecules, multiple copies of the nucleoproteins, and the three subunits of the viral polymerase holding the ends of the viral RNAs. The N-terminal domain of M1 refers to amino acids 1 to about amino acid 20 of the M1 protein.

The matrix protein M2 is a hydrogen ion channel resulting in dissociation of the matrix and nucleoprotein complex within vacuoles. This ion channel releases the genome enabling viral RNA to enter the nucleus of the infected cell and initiate viral replication. Therapeutic substances against influenza, such as amantadine and rimantadine act by blocking the M2 activity. Influenza B has a counterpart protein known as NB; although there is no sequence similarity between M2 and NB, they are both transmembrane proteins and may share similar function. The extracellular domain of the M2 protein which is a transmembrane protein of influenza A virus, is nearly invariant in all influenza A strains. The N-terminal domain of M2 refers to the amino acid sequence N-terminal to the transmembrane domain.

Table 2 provides an exemplary list of M1 and M2 peptide epitopes that may be used for preparation of the multimeric polypeptides according to the present invention.

TABLE 2

M1 and M2 peptide epitopes

| Epitope Type | Protein residues | Amino Acid Sequence | SEQ ID NO: |
|---|---|---|---|
|  | M2 6-9 | EVET | 1 |
| Th | M2 1-15 | MSLLTEVETHTRNGW | 2 |
|  | M2 10-18 | PIRNEWGCR | 3 |
|  | M2 8-15 | ETPIRNEWGC | 4 |
|  | M2 10-20 | PIRNEWGCRCN | 5 |
| CTL | M2 3-11 | LLTEVETPI | 6 |
| CTL | M2 2-10 | SLLTEVETP | 7 |
| CTL | M2 2-11 | SLLTEVETPI | 8 |
| CTL | M2 4-11 | LTEVETPLT | 9 |
| Th | M2 1-15 | MSLLTEVETPIRNEW | 10 |
| Th | M2 1-18 | MSLLTEVETPIRNEWGCR | 11 |
| Th | M2 1-15 | MSLLTEVETLTKNGW | 12 |
| Th | M2 1-15 | MSLLTEVETLTRNGW | 13 |
| CTL | M2 4-12 | LTEVETPIR | 14 |
| CTL | M2 4-13 | LTEVETPIRN | 15 |
| CTL | M2 6-14 | EVETPIRNE | 16 |
| CTL | M2 6-15 | EVETPIRNEW | 17 |
| CTL | M2 4-14 | LTEVETPIRNE | 18 |

TABLE 2-continued

M1 and M2 peptide epitopes

| Epitope Type | Protein residues | Amino Acid Sequence | SEQ ID NO: |
|---|---|---|---|
| Th | M2 4-18 | LTEVETPIRNEWGCR | 19 |
| B cell | M2 6-13 | EVETPIRN | 20 |
| B cell | M2 1-18 | MSLLTEVETPTRNEWECR | 21 |
| B cell | M2 2-24 | SLLTEVETPTRNEWECRCSDSSD | 22 |
| B cell | M2 2-24 | SLLTEVETPIRNEWGCRCNDSSD | 23 |
| B cell | M2 7-15 | VETPIRNEW | 24 |
| B cell | M1 2-12 | SLLTEVETYVL | 25 |
| CTL | M1 2-12 | SLLTEVETYVP | 26 |
| CTL | M1 3-11 | LLTEVETYV | 27 |
| CTL | M1 13-21 | SIVPSGPL | 28 |
| CTL | M1 17-31 | SGPLKAEIAQRLEDV | 29 |
| CTL | M1 18-29 | GPLKAEIAQRLE | 30 |
| CTL | M1 27-35 | RLEDVFAGK | 31 |
| CTL | M1 41-51 | ALMEWLKTRPI | 32 |
| CTL | M1 50-59 | PILSPLTKGI | 33 |
| CTL | M1 51-59 | ILSPLTKGI | 34 |
| CTL | M1 55-73 | LTKGILGFVFTLTVPSERG | 35 |
| CTL | M1 56-68 | TKGILGFVFTLTV | 36 |
| CTL | M1 57-68 | KGILGFVFTLTV | 37 |
| CTL | M1 58-66 | GILGFVFTL | 38 |
| CTL | M1 60-68 | LGFVFTLTV | 39 |
| CTL | M1 59-67 | ILGFVFTLT | 40 |
| CTL | M1 128-135 | ASCMGLIY | 41 |
| CTL | M1 134-142 | RMGAVTTEV | 42 |
| CTL | M1 145-155 | GLVCATCEQIA | 43 |
| CTL | M1 164-172 | QMVATTNPL | 44 |
| CTL | M1 164-173 | QMVATTNPLI | 45 |
| CTL | M1 178-187 | RMVLASTTAK | 46 |
| CTL | M1 232-240 | DLLENLQTY | 47 |

Nucleoprotein (NP) is one of the groups of specific antigens, which distinguishes between influenza A, B and C viruses. In contrast to HA, NP is highly conserved, being 94% conserved in all influenza A viruses. Influenza A virus NP-specific antibody has no virus neutralizing activity, but NP is an important target for cytotoxic T lymphocytes (CTL) which are cross-reactive with all type A viruses (Townsend, J Exp Med 1984 160(2):552-63). CTLs recognize short synthetic peptides corresponding to linear regions of the influenza NP molecule.

Hemagglutinin (HA) is a glycoprotein trimer embedded in the influenza envelope. It has responsible for the attachment and penetration of the virus to the host cell. Antibodies to the HA neutralize viral infectivity. Antigenic variations of this molecule are responsible for frequent outbreaks of influenza and for the poor control of infection by immunization (Ada and Jones, Curr Top Microbial Immunol 1986; 128:1-54).

The influenza virus RNA polymerase is a heterocomplex composed of the three polymerase (P) proteins PB1, PB2 and PA-present in a 1:1:1 ratio. Their role in influenza virulence has not been fully elucidated. Non-limiting examples of HA, NP, PB1 and PB2 peptide epitopes are listed in table 3.

TABLE 3

HA, NP and PB peptide epitopes.

| Epitope Type | Protein residues | Amino Acid Sequence | SEQ ID NO: |
|---|---|---|---|
| B cell | HA 91-108 | SKAYSNCYPYDVPDYASL | 48 |
| B cell | HA 91-108 | SKAFSNCYPYDVPDYASL | 49 |
| B cell | HA 107-124 | STAYSNCYPYDVPDYASL | 50 |
| B cell | HA 143-149 | WTGVTQN | 51 |
| B cell | HA 150-159 | WLTGKNGLYP | 52 |
| B cell | HA 166-175 | WLTEKEGSYP | 53 |
| Th | HA 306-324 | PKYVKQNTLKLATGMRNVP | 54 |
| CTL | HA 521-531 | GVKLESMGIYQ | 55 |
| CTL | HA 518-528 | EISGVKLESMG | 56 |
| CTL | HA 458-467 | NVKNLYEKVK | 57 |
| Th | HA 128-145 | KVKILPKDRWTQHTTTGG | 58 |
| Th | HA 307-319 | PKYVKQNTLKLAT | 59 |
| Th | NP 91-99 | KTGGPIYRR | 60 |
| CTL | NP 44-52 | CTELKLSDY | 61 |
| CTL | NP 82-95 | HPSAGKDPKKTGGP | 62 |
| CTL | NP 82-94 | HPSAGKDPKKTGG | 63 |
| Th | NP 206-229 | FWRGENGRKTRSAYERMCNILKGK | 64 |
| CTL | NP 265-273 | ILRGSVAHK | 65 |
| CTL | NP 305-313 | KLLQNSQVY | 66 |
| CTL | NP 335-349 | SAAFEDLRVLSFIRG | 67 |
| CTL | NP 335-350 | SAAFEDLRVSSFIRGT | 68 |
| CTL | NP 335-350 | SAAFEDLRVLSFIRGY | 69 |
| CTL | NP 380-393 | ELRSRYWAIRTRSG | 70 |
| CTL | NP 380-388 | ELRSRYWAI | 71 |
| CTL | NP 383-391 | SRYWAIRTR | 72 |
| CTL | NP 384-394 | YWAIRTRSGG | 73 |
| CTL | NP 382-390 | SRYWAIRTR | 74 |
| CTL | NP 418-426 | LPFDKPTIM | 75 |
| CTL | PB1 591-599 | VSDGGPNLY | 76 |
| CTL | PB1 571-579 | RRSFELKKL | 77 |

TABLE 3-continued

HA, NP and PB peptide epitopes.

| Epitope Type | Protein residues | Amino Acid Sequence | SEQ ID NO: |
|---|---|---|---|
| CTL | PB2 368-376 | RRATAILRK | 78 |
| CTL(flu B) | NP 30-38 | RPIIRPATL | 79 |
| CTL(flu B) | NP 263-271 | ADRGLLRDI | 80 |
| Th (flu B) | HA 308-320 | PYYTGEHAKAIGN | 81 |
| B (flu B) | HA 354-372 | PAKLLKERGFFGAIAGFLE | 82 |

Chimeric or Recombinant Molecules

A "chimeric protein", "chimeric polypeptide" or "recombinant protein" are used interchangeably and refer to an influenza multimeric polypeptide operatively linked to a polypeptide other than the polypeptide from which the peptide epitope was derived. The multimeric multiepitope polypeptides of the present invention can be prepared by expression in an expression vector per se or as a chimeric protein. The methods to produce a chimeric or recombinant protein comprising one or more influenza peptide epitopes are known to those with skill in the art. A nucleic acid sequence encoding one or more influenza peptide epitopes can be inserted into an expression vector for preparation of a polynucleotide construct for propagation and expression in host cells. A nucleic acid construct encoding a polypeptide comprising multiple repeats of several epitopes, such as a multimeric multiepitope polypeptide, can be prepared by ligation of smaller polynucleotide constructs bearing appropriated restriction sites at their 3' and 5' ends.

In a non-limiting example, the chimeric polypeptide of the present invention includes chimeras of an influenza peptide epitope with one of the following polypeptides: flagellin, Cholera toxin, Tetanus toxin, Ovalbumin, Tuberculosis heat shock protein, Diphtheria Toxoid, Protein G from respiratory syncytial virus, Outer Membrane Protein from *Neisseria meningitides*, nucleoprotein of vesicular stomatitis virus, glycoprotein of vesicular stomatitis virus, *Plasmodium falciparum* Antigen Glutamate-Rich Protein, Merozoite Surface Protein 3 or Viruses envelope protein.

The term "expression vector" and "recombinant expression vector" as used herein refers to a DNA molecule, for example a plasmid, flagellin or virus, containing a desired and appropriate nucleic acid sequences necessary for the expression of the recombinant peptide epitopes for expression in a particular host cell. As used herein "operably linked" refers to a functional linkage of at least two sequences. Operably linked includes linkage between a promoter and a second sequence, for example an nucleic acid of the present invention, wherein the promoter sequence initiates and mediates transcription of the DNA sequence corresponding to the second sequence.

The regulatory regions necessary for transcription of the peptide epitopes can be provided by the expression vector. The precise nature of the regulatory regions needed for gene expression may vary among vectors and host cells. Generally, a promoter is required which is capable of binding RNA polymerase and promoting the transcription of an operably-associated nucleic acid sequence. Regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites. A translation initiation codon (ATG) may also be provided.

In order to clone the nucleic acid sequences into the cloning site of a vector, linkers or adapters providing the appropriate compatible restriction sites are added during synthesis of the nucleic acids. For example, a desired restriction enzyme site can be introduced into a fragment of DNA by amplification of the DNA by use of PCR with primers containing the desired restriction enzyme site.

An expression construct comprising a peptide epitope sequence operably associated with regulatory regions can be directly introduced into appropriate host cells for expression and production of the multimeric multiepitope polypeptide per se or as recombinant fusion proteins. The expression vectors that may be used include but are not limited to plasmids, cosmids, phage, phagemids, flagellin or modified viruses. Typically, such expression vectors comprise a functional origin of replication for propagation of the vector in an appropriate host cell, one or more restriction endonuclease sites for insertion of the desired gene sequence, and one or more selection markers.

The recombinant polynucleotide construct comprising the expression vector and a multimeric polypeptide should then be transferred into a bacterial host cell where it can replicate and be expressed. This can be accomplished by methods known in the art. The expression vector is used with a compatible prokaryotic or eukaryotic host cell which may be derived from bacteria, yeast, insects, mammals and humans.

According to one non limiting example the expression vector is a flagellin vector, for example as disclosed in U.S. Pat. No. 6,130,082. According to other specific embodiments the plasmid vector contains the fliC flagellin gene with unique restriction sites, wherein the multimeric polypeptide is inserted within the hypervariable region of the flagellin and the recombinant flagellin fusion protein containing the multi-epitope polypeptide is expressed in flagella-deficient mutant *Salmonella* or *E. Coli*. The host cells which express the recombinant flagellin fusion protein can be formulated as live vaccines.

Production of the Multimeric Polypeptide

Once expressed by the host cell, the multimeric polypeptide can be separated from undesired components by a number of protein purification methods. One such method uses a polyhistidine tag on the recombinant protein. A polyhistidine-tag consists in at least six histidine (His) residues added to a recombinant protein, often at the N- or C-terminus. Polyhistidine-tags are often used for affinity purification of polyhistidine-tagged recombinant proteins that are expressed in *E. coli* or other prokaryotic expression systems. The bacterial cells are harvested by centrifugation and the resulting cell pellet can be lysed by physical means or with detergents or enzymes such as lysozyme. The raw lysate contains at this stage the recombinant protein among several other proteins derived from the bacteria and are incubated with affinity media such as NTA-agarose, HisPur resin or Talon resin. These affinity media contain bound metal ions, either nickel or cobalt to which the polyhistidine-tag binds with micromolar affinity. The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole. The polyhistidine tag may be subsequently removed using restriction enzymes, endoproteases or exoproteases. Kits for the purification of histidine-tagged proteins can be purchased for example from Qiagen.

Another method is through the production of inclusion bodies, which are inactive aggregates of protein that may form when a recombinant polypeptide is expressed in a prokaryote. While the cDNA may properly code for a translatable mRNA, the protein that results may not fold correctly, or the hydrophobicity of the added peptide epitopes may cause the recombinant polypeptide to become insoluble. Inclusion bodies are easily purified by methods well known in the art. Various procedures for the purification of inclusion bodies are known in the art. In some embodiments the inclusion bodies are recovered from bacterial lysates by centrifugation and are washed with detergents and chelating agents to remove as much bacterial protein as possible from the aggregated recombinant protein. To obtain soluble protein, the washed inclusion bodies are dissolved in denaturing agents and the released protein is then refolded by gradual removal of the denaturing reagents by dilution or dialysis (as described for example in Molecular cloning: a laboratory manual, 3rd edition, Sambrook, J. and Russell, D. W., 2001; CSHL Press).

Alternatively, the recombinant flagellin fusion protein retains the ability to form intact flagella. Various procedures for the purification of the intact flagella are known the art. In one embodiment, the recombinant flagellin molecules expressed by a parental, flagellin-deficient nonmotile strain of bacteria produce functional flagella.

Vaccine Formulation

The vaccines of the present invention comprise a multi-epitope polypeptide or a recombinant fusion protein comprising a multi-epitope polypeptide, and optionally, an adjuvant. The vaccine can be formulated for administration in one of many different modes. According to one embodiment of the invention, the vaccine is administered intranasally. The vaccine formulation may be applied to the lymphatic tissue of the nose in any convenient manner. However, it is preferred to apply it as a liquid stream or liquid droplets to the walls of the nasal passage. The intranasal composition can be formulated, for example, in liquid form as nose drops, spray, or suitable for inhalation, as powder, as cream, or as emulsion. The composition can contain a variety of additives, such as adjuvant, excipient, stabilizers, buffers, or preservatives.

For straightforward application, the vaccine composition is preferably supplied in a vessel appropriate for distribution of the polypeptide or recombinant fusion protein in the form of nose drops or an aerosol. In certain preferred embodiments the vaccine is formulated for mucosal delivery, in particular nasal delivery (Arnon et al., Biologicals. 2001; 29(3-4):237-42; Ben-Yedidia et al., Int Immunol. 1999; 11(7):1043-51).

In another embodiment of the invention, administration is oral and the vaccine may be presented, for example, in the form of a tablet or encased in a gelatin capsule or a microcapsule.

In yet another embodiment, the vaccine is formulated for parenteral administration. In some embodiments the vaccine is formulated for mass inoculation, for example for use with a jet-injector or a single use cartridge. According to yet another embodiment the administration is intramuscular.

According to yet another embodiment the administration is intradermal. Needles specifically designed to deposit the vaccine intradermally are known in the art as disclosed for example in U.S. Pat. Nos. 6,843,781 and 7,250,036 among others. According to other embodiments the administration is performed with a needleless injector.

The formulation of these modalities is general knowledge to those with skill in the art.

Liposomes provide another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 500 µm. Liposomes have been found to be effective in delivering therapeutic agents to dermal and mucosal surfaces. Liposomes can be further modified for targeted delivery by for example, incorporating specific antibodies into the surface membrane, or altered to encapsulate bacteria, viruses or parasites. The average survival time or half life of the intact liposome structure can be extended with the inclusion of certain polymers, for example polyethylene glycol, allowing for prolonged release in vivo. Liposomes may be unilamellar or multilamellar.

The vaccine composition may be formulated by: encapsulating an antigen or an antigen/adjuvant complex in liposomes to form liposome-encapsulated antigen and mixing the liposome-encapsulated antigen with a carrier comprising a continuous phase of a hydrophobic substance. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. Typically, when an adjuvant like alum is used, the adjuvant and the antigen are mixed first to form an antigen/adjuvant complex followed by encapsulation of the antigen/adjuvant complex with liposomes. The resulting liposome-encapsulated antigen is then mixed with the carrier. The term "liposome-encapsulated antigen" may refer to encapsulation of the antigen alone or to the encapsulation of the antigen/adjuvant complex depending on the context. This promotes intimate contact between the adjuvant and the antigen and may, at least in part, account for the immune response when alum is used as the adjuvant. When another is used, the antigen may be first encapsulated in liposomes and the resulting liposome-encapsulated antigen is then mixed into the adjuvant in a hydrophobic substance.

In formulating a vaccine composition that is substantially free of water, antigen or antigen/adjuvant complex is encapsulated with liposomes and mixed with a hydrophobic substance. In formulating a vaccine in an emulsion of water-in-a hydrophobic substance, the antigen or antigen/adjuvant complex is encapsulated with liposomes in an aqueous medium followed by the mixing of the aqueous medium with a hydrophobic substance. In the case of the emulsion, to maintain the hydrophobic substance in the continuous phase, the aqueous medium containing the liposomes may be added in aliquots with mixing to the hydrophobic substance.

In all methods of formulation, the liposome-encapsulated antigen may be freeze-dried before being mixed with the hydrophobic substance or with the aqueous medium as the case may be. In some instances, an antigen/adjuvant complex may be encapsulated by liposomes followed by freeze-drying. In other instances, the antigen may be encapsulated by liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant. Freeze-drying may promote better interaction between the adjuvant and the antigen resulting in a more efficacious vaccine.

Formulation of the liposome-encapsulated antigen into a hydrophobic substance may also involve the use of an emulsifier to promote more even distribution of the liposomes in the hydrophobic substance. Typical emulsifiers are well-known in the art and include mannide oleate (Arlacel™ A), lecithin, Tween™ 80, Spans™ 20, 80, 83 and 85. The emulsifier is used in an amount effective to promote even distribution of the liposomes. Typically, the volume ratio (v/v) of hydrophobic substance to emulsifier is in the range of about 5:1 to about 15:1.

Microparticles and nanoparticles employ small biodegradable spheres which act as depots for vaccine delivery. The major advantage that polymer microspheres possess over other depot-effecting adjuvants is that they are extremely safe and have been approved by the Food and Drug Administration in the US for use in human medicine as suitable sutures and for use as a biodegradable drug delivery system (Langer R. Science. 1990; 249(4976):1527-33). The rates of copolymer hydrolysis are very well characterized, which in turn allows for the manufacture of microparticles with sustained antigen release over prolonged periods of time (O'Hagen, et al., Vaccine. 1993; 11(9):965-9).

Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 μm to 200 μm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers.

In some applications an adjuvant or excipient may be included in the vaccine formulation. Montanide™ (Incomplete Freund's adjuvant) and alum for example, are preferred adjuvants for human use. The choice of the adjuvant will be determined in part by the mode of administration of the vaccine. For example, non-injected vaccination will lead to better overall compliance and lower overall costs. A preferred mode of administration is intramuscular administration. Another preferred mode of administration is intranasal administration. Non-limiting examples of intranasal adjuvants include chitosan powder, PLA and PLG microspheres, QS-21, calcium phosphate nanoparticles (CAP) and mCTA/LTB (mutant cholera toxin E112K with pentameric B subunit of heat labile enterotoxin).

The adjuvant used may also be, theoretically, any of the adjuvants known for peptide- or protein-based vaccines. For example: inorganic adjuvants in gel form (aluminium hydroxide/aluminium phosphate, Warren et al., 1986; calcium phosphate, Relyvelt, 1986); bacterial adjuvants such as monophosphoryl lipid A (Ribi, 1984; Baker et al., 1988) and muramyl peptides (Ellouz et al., 1974; Allison and Byars, 1991; Waters et al., 1986); particulate adjuvants such as the so-called ISCOMS ("immunostimulatory complexes", Mowat and Donachie, 1991; Takahashi et al., 1990; Thapar et al., 1991), liposomes (Mbawuike et al. 1990; Abraham, 1992; Phillips and Emili, 1992; Gregoriadis, 1990) and biodegradable microspheres (Marx et al., 1993); adjuvants based on oil emulsions and emulsifiers such as IFA ("Incomplete Freund's adjuvant" (Stuart-Harris, 1969; Warren et al., 1986), SAF (Allison and Byars, 1991), saponines (such as QS-21; Newman et al., 1992), squalene/squalane (Allison and Byars, 1991); synthetic adjuvants such as non-ionic block copolymers (Hunter et al., 1991), muramyl peptide analogs (Azuma, 1992), synthetic lipid A (Warren et al., 1986; Azuma, 1992), synthetic polynucleotides (Harrington et al., 1978) and polycationic adjuvants (WO 97/30721).

Adjuvants for use with immunogens of the present invention include aluminum or calcium salts (for example hydroxide or phosphate salts). A particularly preferred adjuvant for use herein is an aluminum hydroxide gel such as Alhydrogel™. Calcium phosphate nanoparticles (CAP) is an adjuvant being developed by Biosante, Inc (Lincolnshire, Ill.). The immunogen of interest can be either coated to the outside of particles, or encapsulated inside on the inside [He et al. (November 2000) Clin. Diagn. Lab. Immunol., 7(6):899-903].

Another adjuvant for use with an immunogen of the present invention is an emulsion. A contemplated emulsion can be an oil-in-water emulsion or a water-in-oil emulsion. In addition to the immunogenic chimer protein particles, such emulsions comprise an oil phase of squalene, squalane, peanut oil or the like as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate.

Such emulsions are for example water-in-oil emulsions that comprise squalene, glycerol and a surfactant such as mannide mono-oleate (Arlacel™ A), optionally with squalane, emulsified with the chimer protein particles in an aqueous phase. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France. Other oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. Nos. 4,539,205, 4,643,992, 5,011,828 and 5,093,318. 7-allyl-8-oxoguanosine(loxoribine) has been shown to be particularly effective in inducing an antigen-(immunogen-) specific response.

A useful adjuvant includes monophosphoryl lipid A (MPL®), 3-deacyl monophosphoryl lipid A (3D-MPL®), a well-known adjuvant manufactured by Corixa Corp. of Seattle, formerly Ribi Immunochem, Hamilton, Mont. The adjuvant contains three components extracted from bacteria: monophosphoryl lipid (MPL) A, trehalose dimycolate (TDM) and cell wall skeleton (CWS) (MPL+TDM+CWS) in a 2% squalene/Tween™ 80 emulsion. This adjuvant can be prepared by the methods taught in GB 2122204B.

Other compounds are structurally related to MPL® adjuvant called aminoalkyl glucosamide phosphates (AGPs) such as those available from Corixa Corp under the designation RC-529™ adjuvant {2-[(R)-3-tetra-decanoyloxytetradecanoylamino]-ethyl-2-deoxy-4-O-phosphon-o-3-O—[(R)-3-tetradecanoyloxytetra-decanoyl]-2-[(R)-3-tetra-decanoyloxytet-radecanoyl-amino]-p-D-glucopyranoside triethylammonium salt}. An RC-529 adjuvant is available in a squalene emulsion sold as RC-529SE and in an aqueous formulation as RC-529AF available from Corixa Corp. (see, U.S. Pat. Nos. 6,355,257 and 6,303,347; 6,113,918; and U.S. Publication No. 03-0092643).

Further contemplated adjuvants include synthetic oligonucleotide adjuvants containing the CpG nucleotide motif one or more times (plus flanking sequences) available from Coley Pharmaceutical Group. The adjuvant designated QS21, available from Aquila Biopharmaceuticals, Inc., is an immunologically active saponin fractions having adjuvant activity derived from the bark of the South American tree Quillaja *Saponaria Molina* (e.g. Quil™ A), and the method of its production is disclosed in U.S. Pat. No. 5,057,540. Derivatives of Quil™ A, for example QS21 (an HPLC purified fraction derivative of Quil™ A also known as QA21), and other fractions such as QA17 are also disclosed. Semi-synthetic and synthetic derivatives of Quillaja *Saponaria Molina* saponins are also useful, such as those described in U.S. Pat. Nos. 5,977,081 and 6,080,725. The adjuvant denominated MF59 available from Chiron Corp. is described in U.S. Pat. Nos. 5,709,879 and 6,086,901.

Muramyl dipeptide adjuvants are also contemplated and include N-acetyl-muramyl-L-threonyl-D-isoglutamine (thur-MDP), N-acetyl-nor-muramyl-L-alanyl-D-isoglutamine [CGP 11637, referred to as nor-MDP], and N-acetylmuramyl-L-alanyl-D-isoglutaminyl-L-alanine-2-(1'-2'-dipalmityol-s-n-glycero-3-hydroxyphosphoryloxy) ethylamine [(CGP) 1983A, referred to as MTP-PE]. The so-called muramyl dipeptide analogues are described in U.S. Pat. No. 4,767,842.

Other adjuvant mixtures include combinations of 3D-MPL and QS21 (EP 0 671 948 B1); oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Adjuvant SBAS2 (now ASO2) available from SKB (now Glaxo-SmithKline) contains QS21 and MPL in an oil-in-water emulsion is also useful. Alternative adjuvants include those described in WO 99/52549 and non-particulate suspensions of polyoxyethylene ether (UK Patent Application No. 9807805.8).

The use of an adjuvant that contains one or more agonists for toll-like receptor-4 (TLR-4) such as an MPL® adjuvant or a structurally related compound such as an RC-529® adjuvant or a Lipid A mimetic, alone or along with an agonist for TLR-9 such as a non-methylated oligo deoxynucleotide-containing the CpG motif is also optional.

Another type of adjuvant mixture comprises a stable water-in-oil emulsion further containing aminoalkyl glucosamine phosphates such as described in U.S. Pat. No. 6,113,918. Of the aminoallyl glucosamine phosphates the molecule known as RC-529 {(2-[(R)-3-tetradecanoyloxytetradecanoylamino]ethyl 2-deoxy-4-O-phosphono-3-O-[(R)-3-tetradecanoyloxy-tetradecanoyl]-2-[(R)-3-tetradecanoyloxytetra-decanoylamino]-p-D-glucopyranoside triethylammonium salt.)} is the most preferred. A preferred water-in-oil emulsion is described in WO 9956776.

Adjuvants are utilized in an adjuvant amount, which can vary with the adjuvant, host animal and immunogen. Typical amounts can vary from about 1 mcg to about 1 mg per immunization. Those skilled in the art know that appropriate concentrations or amounts can be readily determined.

Vaccine compositions comprising an adjuvant based on oil in water emulsion is also included within the scope of the present invention. The water in oil emulsion may comprise a metabolisable oil and a saponin, such as for example as described in U.S. Pat. No. 7,323,182. The oil and a saponin are present, for example, in a ratio of between 1:1 and 200:1.

According to several embodiments, the vaccine compositions according to the present invention may contain one or more adjuvants, characterized in that it is present as a solution or emulsion which is substantially free from inorganic salt ions, wherein said solution or emulsion contains one or more water soluble or water-emulsifiable substances which is capable of making the vaccine isotonic or hypotonic. The water soluble or water-emulsifiable substances may be, for example, selected from the group consisting of: maltose; fructose; galactose; saccharose; sugar alcohol; lipid; and combinations thereof.

The formulations of the present invention may optionally comprise a mucosal delivery-enhancing agent such as for example a permeabilizing peptide that reversibly enhances mucosal epithelial paracellular transport by modulating epithelial junctional structure and/or physiology, as described in US 2004/0077540.

The multimeric multiepitope polypeptides of the present invention comprise according to several specific embodiments a proteosome adjuvant. The proteosome adjuvant comprises a purified preparation of outer membrane proteins of meningococci and similar preparations from other bacteria. These proteins are highly hydrophobic, reflecting their role as transmembrane proteins and porins. Due to their hydrophobic protein-protein interactions, when appropriately isolated, the proteins form multi-molecular structures consisting of about 60-100 nm diameter whole or fragmented membrane vesicles. This liposome-like physical state allows the proteosome adjuvant to act as a protein carrier and also to act as an adjuvant.

The use of proteosome adjuvant has been described in the prior art and is reviewed by Lowell G H in "New Generation Vaccines", Second Edition, Marcel Dekker Inc, New York, Basel, Hong. Kong (1997) pages 193-206. Proteosome adjuvant vesicles are described as comparable in size to certain viruses which are hydrophobic and safe for human use. The review describes formulation of compositions comprising non-covalent complexes between various antigens and proteosome adjuvant vesicles which are formed when solubilizing detergent is selectably removed using exhaustive dialysis technology.

The polypeptides of the present invention are optionally complexed to the proteosome antigen vesicles through hydrophobic moieties. For example, an antigen is conjugated to a lipid moiety such as a fatty acyl group. Such a hydrophobic moiety may be linked directly to the multimeric polypeptide or alternatively, a short spacer, for example, of one, two, three or four, up to six or ten amino acids can be used to link the multimeric polypeptide to the fatty group. This hydrophobic anchor interacts with the hydrophobic membrane of the proteosome adjuvant vesicles, while presenting the generally hydrophilic antigenic peptide.

In particular, a hydrophobic anchor may comprise a fatty acyl group attached to the amino terminus or near the carboxyl terminus of the multimeric polypeptide. One example is the twelve-carbon chain lauroyl ($CH_3(CH)_{10}CO$), although any similarly serving fatty acyl group including, but not limited to, acyl groups that are of eight-, ten-, fourteen-, sixteen-, eighteen-, or twenty-carbon chain lengths can also serve as hydrophobic anchors. The anchor may be linked to the peptide antigen using an immunopotentiating spacer. Such a linker may consist of 1-10 amino acids, which may assist in maintaining the conformational structure of the peptide.

The two components, that is the multimeric polypeptide and proteosome adjuvant may be formulated by mixing of the components in a selected solution of detergent(s) and then removing the detergent(s) by diafiltration/ultrafiltration methods. In general, the ratio of proteosome adjuvant to multimeric polypeptide contained in the composition is preferably greater than 1:1 and may be, for example, 1:2, 1:3, 1:4 up to 1:5, 1:10 or 1:20 (by weight). The detergent-based solutions of the two components may contain the same detergent or different detergents and more than one detergent may be present in the mixture subjected to ultrafiltration/diafiltration. Suitable detergents include Triton, Empigen and Mega-10. Other suitable detergents can also be used. The detergents serve to solubilise the components used to prepare the composition.

Vaccines comprising different multimeric polypeptides can be produced by mixing a number of different antigenic peptides with proteosome adjuvant. Alternatively, two or more proteosome adjuvant/antigenic peptide compositions can be produced and subsequently mixed.

Whereas commercial influenza vaccine that are produced in eggs induce allergy in individuals that are sensitive to hen eggs, the multimeric vaccine did not elicit such responses as manifested by IgE titer before and after immunization.

The antigen content is best defined by the biological effect it provokes. Naturally, sufficient antigen should be present to provoke the production of measurable amounts of protective antibody. A convenient test for the biological activity of viruses involves the ability of the antigenic material undergoing testing to deplete a known positive antiserum of its protective antibody. The result is reported in the negative log of the $LD_{50}$ (lethal dose, 50%) for mice treated with virulent organisms which are pretreated with a known antiserum which itself was pretreated with various dilutions of the antigenic material being evaluated. A high value is therefore reflective of a high content of antigenic material which has tied up the antibodies in the known antiserum thus reducing or eliminating the effect of the antiserum on the virulent organism making a small dose lethal. It is preferred that the antigenic material present in the final formulation is at a level sufficient to increase the negative log of $LD_{50}$ by at least 1 preferably 1.4 compared to the result from the virulent organism treated with untreated antiserum. The absolute values obtained for the antiserum control and suitable vaccine material are, of course, dependent on the virulent organism and antiserum standards selected.

The following method may be also used to achieve the ideal vaccine formulation: starting from a defined antigen, which is intended to provoke the desired immune response, in a first step an adjuvant matched to the antigen is found, as described in the specialist literature, particularly in WO 97/30721. In a next step the vaccine is optimized by adding various isotonic-making substances as defined in the present inventions, preferably sugars and/or sugar alcohols, in an isotonic or slightly hypotonic concentration, to the mixture of antigen and adjuvant, with the composition otherwise being identical, and adjusting the solution to a physiological pH in the range from pH 4.0 to 10.0, particularly 7.4. Then, in a first step the substances or the concentration thereof which will improve the solubility of the antigen/adjuvant composition compared with a conventional, saline-buffered solution are determined. The improvement in the solubility characteristics by a candidate substance is a first indication that this substance is capable of bringing about an increase in the immunogenic activity of the vaccine.

Since one of the possible prerequisites for an increase in the cellular immune response is increased binding of the antigen to APCs (antigen presenting cells), in a next step an investigation can be made to see whether the substance leads to an increase of this kind. The procedure used may be analogous to that described in the definition of the adjuvant, e.g. incubating APCs with fluorescence-labelled peptide or protein, adjuvant and isotonic-making substance. An increased uptake or binding of the peptide to APCs brought about by the substance can be determined by comparison with cells which have been mixed with peptide and adjuvant alone or with a peptide/adjuvant composition which is present in conventional saline buffer solution, using throughflow cytometry.

In a second step the candidate substances may be investigated in vitro to see whether and to what extent their presence is able to increase the presentation of a peptide to APCs; the MHC concentration on the cells may be measured using the methods described in WO 97/30721 for testing peptides.

Another possible way of testing the efficiency of a formulation is by using an in vitro model system. In this, APCs are incubated together with adjuvant, peptide and candidate substance and the relative activation of a T-cell clone which specifically recognizes the peptide used is measured (Coligan et al., 1991; Lopez et al., 1993).

The efficiency of the formulation may optionally also be demonstrated by the cellular immune response by detecting a "delayed-type hypersensitivity" (DTH) reaction in immunized animals.

Finally, the immunomodulatory activity of the formulation is measured in animal tests.

The multimeric peptides and polypeptides of the present invention may be synthesized chemically using methods known in the art for synthesis of peptides, peptide multimers and polypeptides. These methods generally rely on the known principles of peptide synthesis; most conveniently, the procedures can be performed according to the known principles of solid phase peptide synthesis.

As used herein "peptide" indicates a sequence of amino acids linked by peptide bonds. The peptides according to the present invention comprise a sequence of 4 to 24 amino acid residues. Multimeric polypeptides comprise at least two repeats and maximum 50 repeats of the peptide epitopes.

Peptide analogs and peptidomimetics are also included within the scope of the invention as well as salts and esters of the peptides of the invention are encompassed. A peptide analog according to the present invention may optionally comprise at least one non-natural amino acid and/or at least one blocking group at either the C terminus or N terminus. Salts of the peptides of the invention are physiologically acceptable organic and inorganic salts. The design of appropriate "analogs" may be computer assisted.

The term "peptidomimetic" means that a peptide according to the invention is modified in such a way that it includes at least one non-peptidic bond such as, for example, urea bond, carbamate bond, sulfonamide bond, hydrazine bond, or any other covalent bond. The design of appropriate "peptidomimetic" may be computer assisted.

Salts and esters of the peptides of the invention are encompassed within the scope of the invention. Salts of the peptides of the invention are physiologically acceptable organic and inorganic salts. Functional derivatives of the peptides of the invention covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide and do not confer toxic properties on compositions containing it. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "amino acid" refers to compounds, which have an amino group and a carboxylic acid group, preferably in a 1,2-1,3-, or 1,4-substitution pattern on a carbon backbone. α-Amino acids are most preferred, and include the 20 natural amino acids (which are L-amino acids except for glycine) which are found in proteins, the corresponding D-amino acids, the corresponding N-methyl amino acids, side chain modified amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, respectively, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a $CHOHCH_2$), reduced amide isosteres (a dipeptide comprising two amino acids wherein the CONH linkage is replaced by a $CH_2NH$ linkage) and thioamide isosteres (a dipeptide comprising two amino acids wherein the CONH linkage is replaced by a CSNH linkage) are also useful residues for this invention.

The amino acids used in this invention are those, which are available commercially or are available by routine synthetic methods. Certain residues may require special methods for incorporation into the peptide, and sequential, divergent or convergent synthetic approaches to the peptide sequence are useful in this invention. Natural coded amino acids and their derivatives are represented by three-letter codes according to IUPAC conventions. When there is no indication, the L isomer was used.

Conservative substitutions of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Multimeric multiepitope polypeptides: examples of multimeric multiepitope polypeptides comprising several repeats of the influenza virus peptide epitopes E1 to E9 listed in Table 1 are presented. The polypeptides include amino acids and short peptides as spacers. The polypeptides are arranged in an alternating sequential polymeric structure or a block copolymer structure. The polypeptides are prepared by expression in an expression vector from a polynucleotide construct comprising various restriction sites for further manipulation of the polypeptide. The polynucleotide construct is supplied from a commercial source.

Vaccines: vaccines prepared from the multimeric multiepitope polypeptides presented in examples 1-3 were used for immunization studies of various mouse strains. Examples for specific vaccines produced and tested are Multimeric #11 is made from the multimeric polypeptide comprising five repeats of nine influenza peptide epitopes arranged in the alternating sequential polymeric structure $[E1E2E3E4E5E6E7E8E9]_5$ presented in example 1.

Multimeric #12 is made from the multimeric polypeptide three repeats of nine influenza peptide epitopes arranged in the alternating sequential polymeric structure $[E1E2E3E4E5E6E7E8E9]_3$ presented in example 3.

Multimeric #14 is made from the multimeric polypeptide comprising three repeats of nine influenza peptide epitopes arranged in the block copolymer structure $[E1]_3$-$[E2]_3$-$[E3]_3$-$[E4]_3$-$[E5]_3$-$[E6]_3$-$[E7]_3$-$[E8]_3$-$[E9]_3$ presented in example 2.

Immunization studies: three strains of mice: an outbred strain (ICR), an inbred strain (BALB/c), and a strain transgenic for human HLA A*0201 molecules (HLA A*0201), were used for immunization studies as well as rabbits in some experiments. Viruses used included the following: A/Texas/1/77, A/Wisconsin/67/05 (WISC), A/WSN/33 (WSN), B/Malaysia/2506/04 (MAL), A/California/07-2007, A/New Caledonia20/99 (NC) and others. All studies were conducted with intramuscular administration of 150 mcg multimeric multiepitope polypeptide in 100 microliters, administered equally to both hind limbs.

Example 1

Multimeric Polypeptide with Five Repeats of a Unit Containing Nine Different Epitopes Arranged in Alternating Sequential Structure This is an example of a multimeric polypeptide comprising five repeats of nine influenza peptide epitopes arranged in the alternating sequential polymeric structure $[E1E2E3E4E5E6E7E8E9]_5$. The estimated molecular weight is 80 kD.

The amino acid sequence of this multimeric polypeptide, including the histidine tag, is shown in FIG. 1B. The DNA sequence of the polynucleotide construct used to prepare this multimeric peptide is shown in FIG. 1A.

Example 2

Multimeric Polypeptide with Three Repeats of Each of Nine Different Epitopes Arranged in Block Copolymer Structure In this example the DNA sequence of a polynucleotide construct used to prepare a multimeric peptide comprising three repeats of nine influenza peptide epitopes arranged in the block copolymer structure [E1]$_3$-[E2]$_3$-[E3]$_3$-[E4]$_3$-[E5]$_3$-[E6]$_3$-[E7]$_3$-[E8]$_3$-[E9]$_3$ is shown in FIG. 2A and the corresponding amino acid sequence is shown in FIG. 2B. The estimated molecular weight is 48 kD.

Example 3

Multimeric Polypeptide with Three Repeats of a Unit Containing Nine Epitopes Arranged in Alternating Sequential Structure This is an example of a multimeric polypeptide comprising three repeats of nine influenza peptide epitopes arranged in the alternating sequential polymeric structure [E1E2E3E4E5E6E7E8E9]$_3$. The estimated molecular weight is 48 kD.

The amino acid sequence of this multimeric polypeptide is shown in FIG. 3B. The DNA sequence of the polynucleotide construct used to prepare this multimeric peptide is shown in FIG. 3A.

Example 4

Cellular Immune Response

The cellular immune responses to two different concentrations of a stimulating influenza virus of the strains A/Texas/1/77, A/WisxWisc/67/05, A/California/07-2007; and B/Malaysia/2506/04, of were evaluated. Transgenic mice (transgenesys for HLA A*0201) mice were vaccinated once with two multimeric vaccines: #11 and #14, emulsified within IFA (Incomplete Freund's adjuvant). 7-10 days after the immunization, their spleen and lymph nodes (LN) were removed and further incubated with the above mentioned viruses. The proliferation was measured by thymidine uptake and is shown in FIG. 4, as the proliferation index for lymphocytes incubated with the stimulating virus. The proliferation was associated with IFN-gamma secretion, in the range of 300-1300 pg/ml. This response is indicating a Th1 cell mediated immune response to the vaccine which could confer a more solid immunity to challenge virus infection.

Example 5

Recognition of Immunizing Antigen and of Viruses by Immune Serum

ICR mice were immunized with the multimeric multiepitope polypeptide comprising five repeats of nine epitopes arranged in the alternating sequential polymeric structure [E1E2E3E4E5E6E7E8E9]$_5$ (Multimeric #11), or with the multimeric multiepitope polypeptide comprising three repeats of nine epitopes arranged in the block copolymer structure [E1]$_3$-[E2]$_3$-[E3]$_3$-[E4]$_3$-[E5]$_3$-[E6]$_3$-[E7]$_3$-[E8]$_3$-[E9]$_3$ (Multimeric #14) suspended in 50% glycerol in PBS, or suspended in IFA as an adjuvant, or with 50% glycerol in PBS as a vehicle control. The recognition of known protective influenza epitopes HA 91-108 and M2 2-12, and of several influenza viruses (WISC, WSN, NC, and MAL), by sera of mice immunized with antigen polypeptide (#11 and #14 respectively), was determined by ELISA and the results are summarized in Tables 4a and 4b. A significant recognition is defined as an at least 4-fold elevation in titer between the pre-immune sera and sera after three IM immunizations at 2-3 weeks intervals.

TABLE 4a

Fold elevation in titer to various antigens of pre-immune sera and sera after 3 immunizations with multimeric multiepitope polypeptide in 50% glycerol in PBS

| | Immunization | | | | | |
|---|---|---|---|---|---|---|
| | #11 in 50% glycerol in PBS | | #14 in 50% glycerol in PBS | | | |
| Mice | ICR | BALB/c | ICR | BALB/c | C57Bl/6j | Rabbits |
| Ab to #11 | 16 | | 64 | | | |
| Ab to #14 | 256 | | 1024 | | | |
| Ab to HA91-108 | 1 | 1 | 64 | 200 | 1600 | 10 |
| Ab to M2 1-18 | 1 | 2 | 64 | 5 | 3 | 1.5 |
| Ab to WISC | | 2 | | 8 | 2 | 2 |
| Ab to WSN | | 4 | | 4 | 2 | 2 |
| Ab to NC | | ND | | 8 | 8 | 2 |
| Ab to MAL | | 2 | | 4 | 2 | 2 |

TABLE 4b

Fold elevation in titer to various antigens of pre-immune sera and sera after 3 immunizations with multimeric multiepitope polypeptide in IFA as an adjuvant

| Immunization | #11 in adjuvant | #14 in adjuvant | | |
|---|---|---|---|---|
| Mice | BALB/c | BALB/c | C57Bl/6j | Rabbits |
| Ab to WISC | 4 | 8 | 4 | 8 |
| Ab to WSN | 4 | 8 | 2 | 16 |
| Ab to NC | ND | 8 | 2 | 8 |
| Ab to MAL | 2 | 4 | 2 | 8 |

Both groups shows high recognition of the immunizing antigen, the peptides HA91-108 and M2 2-18 were recognized only by the sera of mice immunized with #14 but not with sera from mice immunized with #11.

Normal human sera could recognize Multimeric vaccine candidates, indicating of potential memory responses to be elicited following immunization of human subjects with this vaccine. Mean titers of 4 human sera to #11 and #14 were 6000 and 6400 respectively.

Example 6

Protection Against a Highly Lethal Challenge with H3N2 A/Texas/1/77

Figure 5:
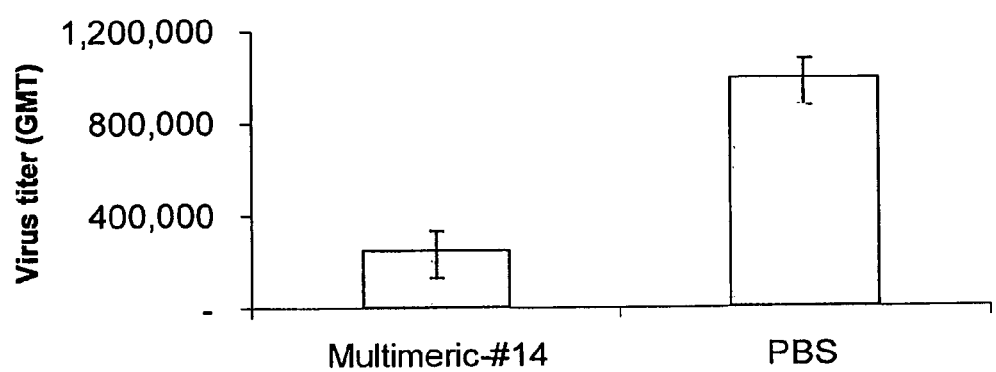

Groups of eight transgenic mice were immunized three times, at 3-week intervals, intramuscularly with the Multimeric-#14 vaccine or with PBS. A challenge infection with a highly lethal dose (300 LD$_{50}$) of H3N2 A/Texas/1/77 was given three weeks after the last boost. Mice were sacrificed five days post infection. A significant reduction of virus titer in mice lungs was observed, as described in FIG. 5, despite of the large amount of virus used for infection.

Example 7

In Vivo Efficacy Studies

Two vaccine versions have been evaluated in vivo: the multimeric polypeptide suspended in 50% Glycerol in PBS or in Incomplete Freund's adjuvant.

The purified vaccine is used in several mice models to establish its efficacy, mechanism of action and preliminary toxicology data prior to the repeated dose toxicology. The humoral response as well as pharmacodynamics studies are performed in several strains of mice. One animal model that is employed for the evaluation of the vaccine is the transgenic mice for HLA A*0201. This model is used for determination of the optimal dose as well as for cellular parameters of the immune response to reveal its mechanism of action.

Example 8

The efficacy of the vaccine was demonstrated in two preliminary studies using ICR and transgenic (HLA A*0201) mice. The mice were vaccinated intramuscularly three times with 3 weeks interval with a dose of 150 mcg/mouse of vaccines #11, #12 and #14 with and without adjuvant (IFA). Three to four weeks after the last immunization, the mice were infected with a 300 LD50 of a mouse adapted influenza virus H3N2 strain (A/Texas/1/77). Five days post infection, the survival rate was monitored. Treated and control groups immunized with 50% glycerol in PBS with and without IFA were compared.

Figure 6A:
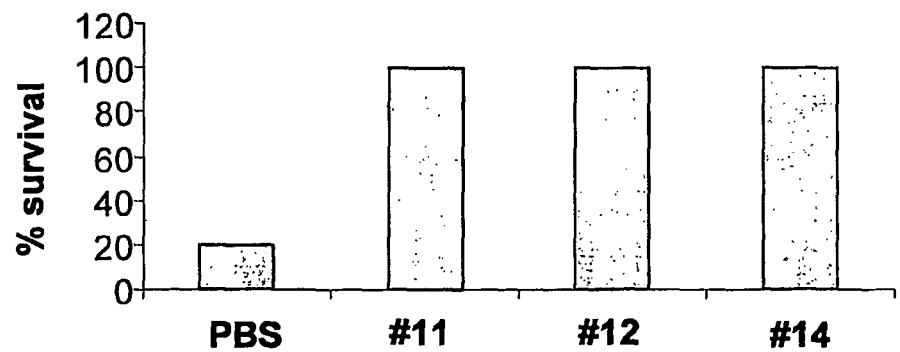

The survival rate (FIG. 6A) following 300 LD50 infection in ICR mice was 100% whereas in the control groups (50% Glycerol in PBS) survival rate of 20% was demonstrated.

Figure 6B:
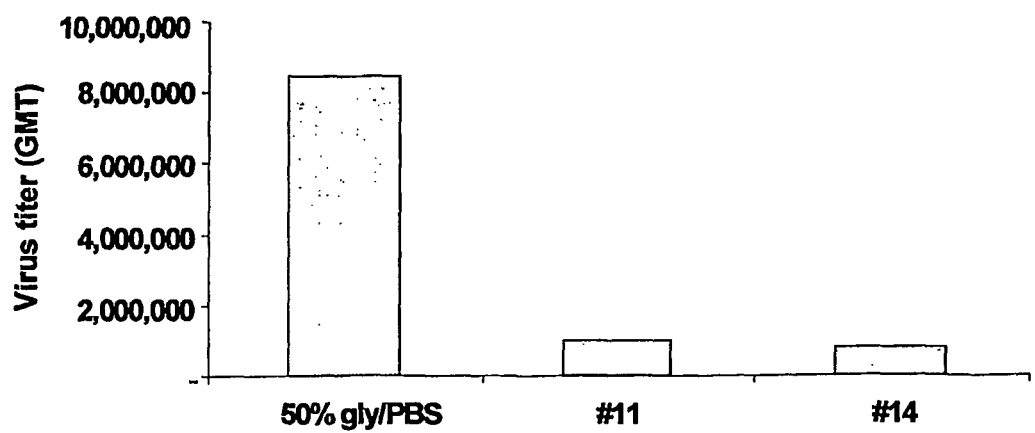

The viral load in their lungs is detailed in FIG. 6B for vaccines #11 and #14 only. The viral load in the groups where 100% survival was found is significantly lower than the viral load in the control groups ($p<0.05$). Due of the small number of mice per group (5 mice), the statistical analysis was done using Two-sided Fisher's Exact Test. P value of 5% or less is considered statistically significant. The data was analyzed using the SAS® version 9.1 (SAS Institute, Cary N.C.).

Figure 7:
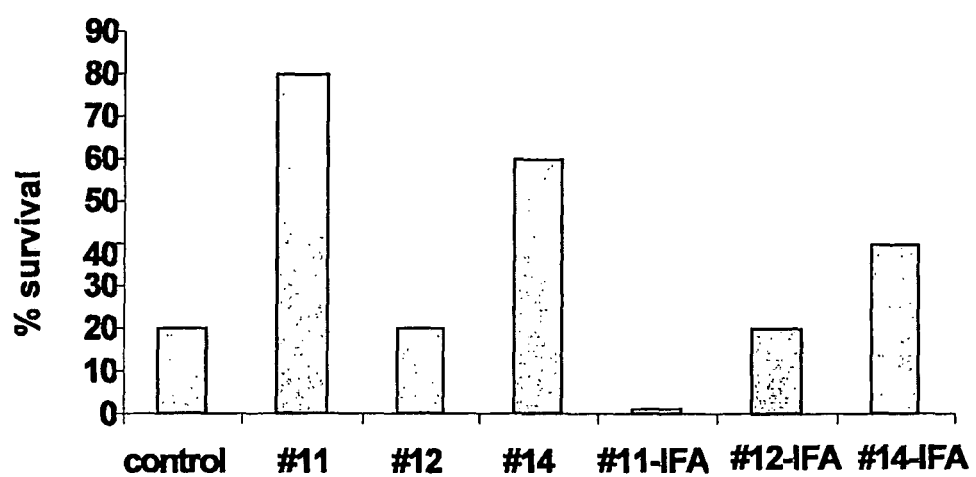

As for the survival in transgenic mice (FIG. 7) immunized with the vaccine in PBS/50% Glycerol, using the same vaccination and infection procedures mentioned above, the survival rates were 80% and 60% to vaccination with #11 and #14 respectively as compare to 20% in control group. Vaccine #12 was not protective in this mouse model as well as the adjuvanted (IFA) vaccines tested. It seems that in this animal model or at least in this study, the addition of adjuvant was unnecessary and even reduced the vaccine protective potential.

Example 9

Repeated Dose Toxicology

Repeated dose toxicology trials are performed with vaccine #14 (Multimeric vaccine in three block repeats suspended in 50% Glycerol in PBS or in Incomplete Freund's adjuvant, according a protocol based on: http://www3.niaid.nih.gov/daids/vaccine/Science/VRTT/06_SafetyTest.htm.

A preliminary dose related toxicology study is performed in ICR outbred mice. Three animals per gender per dose for each time point of sacrifice are employed to test the histopathology of their major organs following intramuscular administration of the vaccine one, two and three times.

The highest-dose intended for the clinic is employed in a 6-week repeat dosing containing three fortnightly vaccinations is likely to be sufficient to assess the toxicity of the product and enable two repeated. The studies include monitoring the in-live stage followed by a full range of toxicological parameters, including necropsy and full histopathological examination of all major organs on days 2 days and 2 weeks post immunization in order to demonstrate that any toxicological effects seen during the treatment period were reversible.

Example 10

Phase I/IIa Clinical Trial

The primary objective of this clinical study is to examine safety of the preventive anti-influenza vaccine after a single or double intramuscular administration. The study is conducted under controlled clinical settings among healthy volunteers aged from 18 years old to 49 years old. The secondary objective is to estimate the immunogenicity induced by administration of the multimeric vaccine. This phase I/II study assesses the most common acute adverse effects and examines the size of doses that patients can take safely without a high incidence of side effects.

Example 11

Anti Viral Response in Mice Sera Immunized with Commercial Influenza Vaccine Followed by Immunization with Multimeric Vaccine Transgenic mice for HLA A*0201 were immunized with the commercial inactivated influenza vaccine (split virion) BP Vaxigrip® three times, on days 0, 60, 81, or with Vaxigrip® once, on day 0, and 2 additional immunizations (on days 60 and 81) with the Multimeric vaccines #11, #12 and #14. Blood collection was performed before immunization (pre immune) and after the last immunization. Antibodies to several influenza strains were determined in pooled sera: H3N2: A/Wisconsin/67/05, A/Texas/1/77, A/California/07/2007, A/Fujian/411/2002, A/Moscow/10/99 and A/Panama/2007/99; H1N1: A/New Caledonia/20/99, A/WSN/33, A/PR8/34

B: B/Malaysia/2506/04, B/Lee/40.

After the first immunization with Vaxigrip®, which is intended for a single immunization in human, there was no significant elevation in titers to all of the viruses (except of ×4 fold titer elevation to A/California).

The results are shown in tables 5A and 5B. With the Multimeric formulations, prior immunization with Vaxigrip® did not significantly elevated the response to the viruses as compared to other data from immunization studies where similar humoral responses were demonstrated. A maximum of 8 times elevation in titers of post/pre immune was observed after two immunizations with the Multimeric vaccine. Control group administered with PBS was negative to all viruses. In the comparison of the different multimeric variants, #14 was the best candidate in terms of humoral response to viruses.

TABLE 5A

H3N2

| Treatment | immune | WISC t | f | Texas t | f | Califor t | f | Fujian t | f | Moscow t | f | Panama t | f |
|---|---|---|---|---|---|---|---|---|---|---|---|---|---|
| 1x Vaxigrip + 2x Multi #11 | 0 | 200 | | 200 | | 800 | | 400 | | 400 | | 400 | |
| | 1 | 400 | 2 | 400 | 2 | 800 | 1 | 800 | 2 | 800 | 2 | 800 | 2 |
| | 2+ | 800 | 4 | 400 | 2 | 3200 | 4 | 800 | 2 | 800 | 2 | 1600 | 4 |
| 1x Vaxigrip + 2x Multi #12 | 0 | 400 | | 200 | | 400 | | 400 | | 800 | | 800 | |
| | 1 | 800 | 2 | 400 | 2 | 1600 | 4 | 400 | 1 | 800 | 1 | 800 | 1 |
| | 2+ | 800 | 2 | 400 | 2 | 3200 | 8 | 1600 | 4 | 1600 | 2 | 3200 | 4 |
| 1x Vaxigrip + 2x Multi #14 | 0 | 200 | | 200 | | 800 | | 400 | | 400 | | 800 | |
| | 1 | 800 | 4 | 400 | 2 | 1600 | 2 | 800 | 2 | 1600 | 4 | 3200 | 4 |
| | 2+ | 1600 | 8 | 1600 | 8 | 3200 | 4 | 1600 | 4 | 3200 | 8 | 6400 | 8 |
| PBS | 1 | 200 | | 100 | | 200 | | 200 | | 200 | | 200 | |
| | 2+ | 200 | 1 | 100 | 1 | 200 | 1 | 200 | 1 | 200 | 1 | 400 | 2 | t = titer,
f = fold

TABLE 5B

H1N1 and Influenza B

| Treatment | immune | NC t | f | WSN t | f | PR8/34 t | f | B/Malaysia t | f | B/Lee t | f |
|---|---|---|---|---|---|---|---|---|---|---|---|
| 1x Vaxigrip + 2x Multi #11 | 0 | 100 | | 200 | | 400 | | 400 | | 200 | |
| | 1 | 400 | 4 | 400 | 2 | 800 | 2 | 1600 | 4 | 400 | 2 |
| | 2+ | 400 | 4 | 800 | 4 | 800 | 2 | 1600 | 4 | 400 | 2 |
| 1x Vaxigrip + 2x Multi #12 | 0 | 200 | | 200 | | 200 | | 800 | | 100 | |
| | 1 | 400 | 2 | 400 | 2 | 400 | 2 | 800 | 1 | 400 | 4 |
| | 2+ | 400 | 2 | 800 | 4 | 400 | 2 | 800 | 1 | 400 | 4 |
| 1x Vaxigrip + 2x Multi #14 | 0 | 100 | | 200 | | 100 | | 200 | | 200 | |
| | 1 | 400 | 4 | 800 | 4 | 400 | 4 | 400 | 2 | 400 | 2 |
| | 2+ | 400 | 4 | 1600 | 8 | 400 | 4 | 1600 | 8 | 400 | 2 |
| PBS | 1 | 100 | | 100 | | 100 | | 100 | | 100 | |
| | 2+ | 100 | 1 | 200 | 2 | 200 | 2 | 200 | 2 | 100 | 1 | t = titer,
f = fold

Example 12

Peptide Synthesis

Peptides and multimeric peptides were synthesized using typical solid phase peptide synthesis with the following materials: Protected amino acids, 9-fluorenylmethyloxycarbonyl-N-hydroxysuccinimide (Fmoc-OSu), bromo-tris-pyrrolidone-phosphonium hexafluorophosphate (PyBrop), Rink amide methylbenzhydrylamine (MBHA) polystyrene resins and many organic and supports for solid phase peptide synthesis (SPPS) were purchased from Nova Biochemicals (Laufelfingen, Switzerland). Bis(trichloromethyl)carbonate (BTC) was purchased from Lancaster (Lancashire, England), Trifluoroacetic acid (TFA) and solvents for high performance liquid chromatography (HPLC) were purchased from Bio-Lab (Jerusalem, Israel).

Solvents for organic chemistry were purchased from Frutarom (Haifa, Israel). Nuclear magnetic resonance (NMR) spectra were recorded on a Bruker AMX-300 MHz spectrometer. Mass spectra were performed on a Finnigan LCQ DUO ion trap mass spectrometer. Thin layer chromatography (TLC) was performed on Merck F245 60 silica gel plates (Darmstadt, Germany). HPLC analysis was performed using a Vydac analytical RP column (C18, 4.6×250 mm, catalog number 201TP54), and were carried out on a Merck-Hitachi L-7100 pump and a Merck-Hitachi L-7400 variable wavelength detector operating at 215 nm. The mobile phase consisted of a gradient system, with solvent A corresponding to water with 0.1% TFA and solvent B corresponding to acetonitrile (ACN) with 0.1% TFA. The mobile phase started with 0.95% A from 0 to 5 min followed by linear gradient from 5% B to 95% B from 5 to 55 min. The gradient remained at 95% B for an additional 5 min, and then was dropped to 95% A and 5% B from 60 to 65 min. The gradient remained at 95% A for additional 5 min to achieve column equilibration. The flow rate of the mobile phase was 1 mL/min. Peptide purification was performed by reversed phase HPLC (RP-HPLC) (on L-6200A pump, Merck-Hitachi, Japan), using a Vydac preparative-RP column (C8, 22×250 mm, catalog number 218TP1022). All preparative HPLC were carried out using a gradient system with solvent A corresponding to water with 0.1% TFA and solvent B corresponding to ACN with 0.1% TFA.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

SEQUENCE LISTING

<160> NUMBER OF SEQ ID NOS: 88

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Glu Val Glu Thr
1

<210> SEQ ID NO 2
<211> LENGTH: 15
<212> TYPE: PRT
<213> ORGANISM: Artificial
<220> FEATURE:
<223> OTHER INFORMATION: Synthetic peptide

<400> SEQUENCE: 2

Met Ser Leu Leu Thr Glu Val Glu Thr His Thr Arg Asn Gly Trp
1               5                   10                  15

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Pro Ile Arg Asn Glu Trp Gly Cys Arg
1               5

<210> SEQ ID NO 4
<211> LENGTH: 10
<212> TYPE: PRT
<213> ORGANISM: Artificial
<220> FEATURE:
<223> OTHER INFORMATION: Synthetic peptide

<400> SEQUENCE: 4

Glu Thr Pro Ile Arg Asn Glu Trp Gly Cys
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic peptide

<400> SEQUENCE: 5

Pro Ile Arg Asn Glu Trp Gly Cys Arg Cys Asn
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic peptide

<400> SEQUENCE: 6

Leu Leu Thr Glu Val Glu Thr Pro Ile

```
1               5

<210> SEQ ID NO 7
<211> LENGTH: 9
<212> TYPE: PRT
<213> ORGANISM: Artificial
<220> FEATURE:
<223> OTHER INFORMATION: Synthetic peptide

<400> SEQUENCE: 7

Ser Leu Leu Thr Glu Val Glu Thr Pro
1               5

<210> SEQ ID NO 8
<211> LENGTH: 10
<212> TYPE: PRT
<213> ORGANISM: Artificial
<220> FEATURE:
<223> OTHER INFORMATION: Synthetic peptide

<400> SEQUENCE: 8

Ser Leu Leu Thr Glu Val Glu Thr Pro Ile
1               5                   10

<210> SEQ ID NO 9
<211> LENGTH: 9
<212> TYPE: PRT
<213> ORGANISM: Artificial
<220> FEATURE:
<223> OTHER INFORMATION: Synthetic peptide

<400> SEQUENCE: 9

Leu Thr Glu Val Glu Thr Pro Leu Thr
1               5

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Met Ser Leu Leu Thr Glu Val Glu Thr Pro Ile Arg Asn Glu Trp
1               5                   10                  15

<210> SEQ ID NO 11
<211> LENGTH: 18
<212> TYPE: PRT
<213> ORGANISM: Artificial
<220> FEATURE:
<223> OTHER INFORMATION: Synthetic peptide

<400> SEQUENCE: 11

Met Ser Leu Leu Thr Glu Val Glu Thr Pro Ile Arg Asn Glu Trp Gly
1               5                   10                  15

Cys Arg

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Met Ser Leu Leu Thr Glu Val Glu Thr Leu Thr Lys Asn Gly Trp
```

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Met Ser Leu Leu Thr Glu Val Glu Thr Leu Thr Arg Asn Gly Trp
1               5                   10                  15

<210> SEQ ID NO 14
<211> LENGTH: 9
<212> TYPE: PRT
<213> ORGANISM: Artificial
<220> FEATURE:
<223> OTHER INFORMATION: Synthetic peptide

<400> SEQUENCE: 14

Leu Thr Glu Val Glu Thr Pro Ile Arg
1               5

<210> SEQ ID NO 15
<211> LENGTH: 10
<212> TYPE: PRT
<213> ORGANISM: Artificial
<220> FEATURE:
<223> OTHER INFORMATION: Synthetic peptide

<400> SEQUENCE: 15

Leu Thr Glu Val Glu Thr Pro Ile Arg Asn
1               5                   10

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

Glu Val Glu Thr Pro Ile Arg Asn Glu
1               5

<210> SEQ ID NO 17
<211> LENGTH: 10
<212> TYPE: PRT
<213> ORGANISM: Artificial
<220> FEATURE:
<223> OTHER INFORMATION: Synthetic peptide

<400> SEQUENCE: 17

Glu Val Glu Thr Pro Ile Arg Asn Glu Trp
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic peptide

<400> SEQUENCE: 18

Leu Thr Glu Val Glu Thr Pro Ile Arg Asn Glu
1               5                   10

```
<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Leu Thr Glu Val Glu Thr Pro Ile Arg Asn Glu Trp Gly Cys Arg
1               5                   10                  15

<210> SEQ ID NO 20
<211> LENGTH: 8
<212> TYPE: PRT
<213> ORGANISM: Artificial
<220> FEATURE:
<223> OTHER INFORMATION: Synthetic peptide

<400> SEQUENCE: 20

Glu Val Glu Thr Pro Ile Arg Asn
1               5

<210> SEQ ID NO 21
<211> LENGTH: 18
<212> TYPE: PRT
<213> ORGANISM: Artificial
<220> FEATURE:
<223> OTHER INFORMATION: Synthetic peptide

<400> SEQUENCE: 21

Met Ser Leu Leu Thr Glu Val Glu Thr Pro Thr Arg Asn Glu Trp Glu
1               5                   10                  15

Cys Arg

<210> SEQ ID NO 22
<211> LENGTH: 23
<212> TYPE: PRT
<213> ORGANISM: Artificial
<220> FEATURE:
<223> OTHER INFORMATION: Synthetic peptide

<400> SEQUENCE: 22

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 23
<211> LENGTH: 23
<212> TYPE: PRT
<213> ORGANISM: Artificial
<220> FEATURE:
<223> OTHER INFORMATION: Synthetic peptide

<400> SEQUENCE: 23

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 24
<211> LENGTH: 9
<212> TYPE: PRT
<213> ORGANISM: Artificial
<220> FEATURE:
<223> OTHER INFORMATION: Synthetic peptide
```

```
<400> SEQUENCE: 24

Val Glu Thr Pro Ile Arg Asn Glu Trp
1               5

<210> SEQ ID NO 25
<211> LENGTH: 11
<212> TYPE: PRT
<213> ORGANISM: Artificial
<220> FEATURE:
<223> OTHER INFORMATION: Synthetic peptide

<400> SEQUENCE: 25

Ser Leu Leu Thr Glu Val Glu Thr Tyr Val Leu
1               5                   10

<210> SEQ ID NO 26
<211> LENGTH: 11
<212> TYPE: PRT
<213> ORGANISM: Artificial
<220> FEATURE:
<223> OTHER INFORMATION: Synthetic peptide

<400> SEQUENCE: 26

Ser Leu Leu Thr Glu Val Glu Thr Tyr Val Pro
1               5                   10

<210> SEQ ID NO 27
<211> LENGTH: 9
<212> TYPE: PRT
<213> ORGANISM: Artificial
<220> FEATURE:
<223> OTHER INFORMATION: Synthetic peptide

<400> SEQUENCE: 27

Leu Leu Thr Glu Val Glu Thr Tyr Val
1               5

<210> SEQ ID NO 28
<211> LENGTH: 8
<212> TYPE: PRT
<213> ORGANISM: Artificial
<220> FEATURE:
<223> OTHER INFORMATION: Synthetic peptide

<400> SEQUENCE: 28

Ser Ile Val Pro Ser Gly Pro Leu
1               5

<210> SEQ ID NO 29
<211> LENGTH: 15
<212> TYPE: PRT
<213> ORGANISM: Artificial
<220> FEATURE:
<223> OTHER INFORMATION: Synthetic peptide

<400> SEQUENCE: 29

Ser Gly Pro Leu Lys Ala Glu Ile Ala Gln Arg Leu Glu Asp Val
1               5                   10                  15

<210> SEQ ID NO 30
<211> LENGTH: 12
<212> TYPE: PRT
<213> ORGANISM: Artificial
<220> FEATURE:
<223> OTHER INFORMATION: Synthetic peptide

<400> SEQUENCE: 30
```

```
Gly Pro Leu Lys Ala Glu Ile Ala Gln Arg Leu Glu
1               5                   10
```

<210> SEQ ID NO 31
<211> LENGTH: 9
<212> TYPE: PRT
<213> ORGANISM: Artificial
<220> FEATURE:
<223> OTHER INFORMATION: Synthetic peptide

<400> SEQUENCE: 31

```
Arg Leu Glu Asp Val Phe Ala Gly Lys
1               5
```

<210> SEQ ID NO 32
<211> LENGTH: 11
<212> TYPE: PRT
<213> ORGANISM: Artificial
<220> FEATURE:
<223> OTHER INFORMATION: Synthetic peptide

<400> SEQUENCE: 32

```
Ala Leu Met Glu Trp Leu Lys Thr Arg Pro Ile
1               5                   10
```

<210> SEQ ID NO 33
<211> LENGTH: 10
<212> TYPE: PRT
<213> ORGANISM: Artificial
<220> FEATURE:
<223> OTHER INFORMATION: Synthetic peptide

<400> SEQUENCE: 33

```
Pro Ile Leu Ser Pro Leu Thr Lys Gly Ile
1               5                   10
```

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

```
Ile Leu Ser Pro Leu Thr Lys Gly Ile
1               5
```

<210> SEQ ID NO 35
<211> LENGTH: 19
<212> TYPE: PRT
<213> ORGANISM: Artificial
<220> FEATURE:
<223> OTHER INFORMATION: Synthetic peptide

<400> SEQUENCE: 35

```
Leu Thr Lys Gly Ile Leu Gly Phe Val Phe Thr Leu Thr Val Pro Ser
1               5                   10                  15

Glu Arg Gly
```

<210> SEQ ID NO 36
<211> LENGTH: 13
<212> TYPE: PRT
<213> ORGANISM: Artificial
<220> FEATURE:
<223> OTHER INFORMATION: Synthetic peptide

<400> SEQUENCE: 36

-continued

```
Thr Lys Gly Ile Leu Gly Phe Val Phe Thr Leu Thr Val
1               5                   10

<210> SEQ ID NO 37
<211> LENGTH: 12
<212> TYPE: PRT
<213> ORGANISM: Artificial
<220> FEATURE:
<223> OTHER INFORMATION: Synthetic peptide

<400> SEQUENCE: 37

Lys Gly Ile Leu Gly Phe Val Phe Thr Leu Thr Val
1               5                   10

<210> SEQ ID NO 38
<211> LENGTH: 9
<212> TYPE: PRT
<213> ORGANISM: Artificial
<220> FEATURE:
<223> OTHER INFORMATION: Synthetic peptide

<400> SEQUENCE: 38

Gly Ile Leu Gly Phe Val Phe Thr Leu
1               5

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39

Leu Gly Phe Val Phe Thr Leu Thr Val
1               5

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

Ile Leu Gly Phe Val Phe Thr Leu Thr
1               5

<210> SEQ ID NO 41
<211> LENGTH: 8
<212> TYPE: PRT
<213> ORGANISM: Artificial
<220> FEATURE:
<223> OTHER INFORMATION: Synthetic peptide

<400> SEQUENCE: 41

Ala Ser Cys Met Gly Leu Ile Tyr
1               5

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

Arg Met Gly Ala Val Thr Thr Glu Val
```

-continued

```
<210> SEQ ID NO 43
<211> LENGTH: 11
<212> TYPE: PRT
<213> ORGANISM: Artificial
<220> FEATURE:
<223> OTHER INFORMATION: Synthetic peptide

<400> SEQUENCE: 43

Gly Leu Val Cys Ala Thr Cys Glu Gln Ile Ala
1               5                   10

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

Gln Met Val Ala Thr Thr Asn Pro Leu
1               5

<210> SEQ ID NO 45
<211> LENGTH: 10
<212> TYPE: PRT
<213> ORGANISM: Artificial
<220> FEATURE:
<223> OTHER INFORMATION: Synthetic peptide

<400> SEQUENCE: 45

Gln Met Val Ala Thr Thr Asn Pro Leu Ile
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic peptide

<400> SEQUENCE: 46

Arg Met Val Leu Ala Ser Thr Thr Ala Lys
1               5                   10

<210> SEQ ID NO 47
<211> LENGTH: 9
<212> TYPE: PRT
<213> ORGANISM: Artificial
<220> FEATURE:
<223> OTHER INFORMATION: Synthetic peptide

<400> SEQUENCE: 47

Asp Leu Leu Glu Asn Leu Gln Thr Tyr
1               5

<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Ser Lys Ala Tyr Ser Asn Cys Tyr Pro Tyr Asp Val Pro Asp Tyr Ala
1               5                   10                  15
```

Ser Leu

<210> SEQ ID NO 49
<211> LENGTH: 18
<212> TYPE: PRT
<213> ORGANISM: Artificial
<220> FEATURE:
<223> OTHER INFORMATION: Synthetic peptide

<400> SEQUENCE: 49

Ser Lys Ala Phe Ser Asn Cys Tyr Pro Tyr Asp Val Pro Asp Tyr Ala
1               5                   10                  15
Ser Leu

<210> SEQ ID NO 50
<211> LENGTH: 18
<212> TYPE: PRT
<213> ORGANISM: Artificial
<220> FEATURE:
<223> OTHER INFORMATION: Synthetic peptide

<400> SEQUENCE: 50

Ser Thr Ala Tyr Ser Asn Cys Tyr Pro Tyr Asp Val Pro Asp Tyr Ala
1               5                   10                  15
Ser Leu

<210> SEQ ID NO 51
<211> LENGTH: 7
<212> TYPE: PRT
<213> ORGANISM: Artificial
<220> FEATURE:
<223> OTHER INFORMATION: Synthetic peptide

<400> SEQUENCE: 51

Trp Thr Gly Val Thr Gln Asn
1               5

<210> SEQ ID NO 52
<211> LENGTH: 10
<212> TYPE: PRT
<213> ORGANISM: Artificial
<220> FEATURE:
<223> OTHER INFORMATION: Synthetic peptide

<400> SEQUENCE: 52

Trp Leu Thr Gly Lys Asn Gly Leu Tyr Pro
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic peptide

<400> SEQUENCE: 53

Trp Leu Thr Glu Lys Glu Gly Ser Tyr Pro
1               5                   10

<210> SEQ ID NO 54
<211> LENGTH: 19
<212> TYPE: PRT
<213> ORGANISM: Artificial
<220> FEATURE:
<223> OTHER INFORMATION: Synthetic peptide

<400> SEQUENCE: 54

Pro Lys Tyr Val Lys Gln Asn Thr Leu Lys Leu Ala Thr Gly Met Arg
1               5                   10                  15

Asn Val Pro

<210> SEQ ID NO 55
<211> LENGTH: 11
<212> TYPE: PRT
<213> ORGANISM: Artificial
<220> FEATURE:
<223> OTHER INFORMATION: Synthetic peptide

<400> SEQUENCE: 55

Gly Val Lys Leu Glu Ser Met Gly Ile Tyr Gln
1               5                   10

<210> SEQ ID NO 56
<211> LENGTH: 11
<212> TYPE: PRT
<213> ORGANISM: Artificial
<220> FEATURE:
<223> OTHER INFORMATION: Synthetic peptide

<400> SEQUENCE: 56

Glu Ile Ser Gly Val Lys Leu Glu Ser Met Gly
1               5                   10

<210> SEQ ID NO 57
<211> LENGTH: 10
<212> TYPE: PRT
<213> ORGANISM: Artificial
<220> FEATURE:
<223> OTHER INFORMATION: Synthetic peptide

<400> SEQUENCE: 57

Asn Val Lys Asn Leu Tyr Glu Lys Val Lys
1               5                   10

<210> SEQ ID NO 58
<211> LENGTH: 18
<212> TYPE: PRT
<213> ORGANISM: Artificial
<220> FEATURE:
<223> OTHER INFORMATION: Synthetic peptide

<400> SEQUENCE: 58

Lys Val Lys Ile Leu Pro Lys Asp Arg Trp Thr Gln His Thr Thr Thr
1               5                   10                  15

Gly Gly

<210> SEQ ID NO 59
<211> LENGTH: 13
<212> TYPE: PRT
<213> ORGANISM: Artificial
<220> FEATURE:
<223> OTHER INFORMATION: Synthetic peptide

<400> SEQUENCE: 59

Pro Lys Tyr Val Lys Gln Asn Thr Leu Lys Leu Ala Thr
1               5                   10

<210> SEQ ID NO 60
<211> LENGTH: 9
<212> TYPE: PRT
<213> ORGANISM: Artificial
<220> FEATURE:
<223> OTHER INFORMATION: Synthetic peptide

```
<400> SEQUENCE: 60

Lys Thr Gly Gly Pro Ile Tyr Arg Arg
1               5

<210> SEQ ID NO 61
<211> LENGTH: 9
<212> TYPE: PRT
<213> ORGANISM: Artificial
<220> FEATURE:
<223> OTHER INFORMATION: Synthetic peptide

<400> SEQUENCE: 61

Cys Thr Glu Leu Lys Leu Ser Asp Tyr
1               5

<210> SEQ ID NO 62
<211> LENGTH: 14
<212> TYPE: PRT
<213> ORGANISM: Artificial
<220> FEATURE:
<223> OTHER INFORMATION: Synthetic peptide

<400> SEQUENCE: 62

His Pro Ser Ala Gly Lys Asp Pro Lys Thr Gly Gly Pro
1               5                   10

<210> SEQ ID NO 63
<211> LENGTH: 13
<212> TYPE: PRT
<213> ORGANISM: Artificial
<220> FEATURE:
<223> OTHER INFORMATION: Synthetic peptide

<400> SEQUENCE: 63

His Pro Ser Ala Gly Lys Asp Pro Lys Thr Gly Gly
1               5                   10

<210> SEQ ID NO 64
<211> LENGTH: 24
<212> TYPE: PRT
<213> ORGANISM: Artificial
<220> FEATURE:
<223> OTHER INFORMATION: Synthetic peptide

<400> SEQUENCE: 64

Phe Trp Arg Gly Glu Asn Gly Arg Lys Thr Arg Ser Ala Tyr Glu Arg
1               5                   10                  15

Met Cys Asn Ile Leu Lys Gly Lys
            20

<210> SEQ ID NO 65
<211> LENGTH: 9
<212> TYPE: PRT
<213> ORGANISM: Artificial
<220> FEATURE:
<223> OTHER INFORMATION: Synthetic peptide

<400> SEQUENCE: 65

Ile Leu Arg Gly Ser Val Ala His Lys
1               5

<210> SEQ ID NO 66
<211> LENGTH: 9
<212> TYPE: PRT
<213> ORGANISM: Artificial
<220> FEATURE:
```

<223> OTHER INFORMATION: Synthetic peptide

<400> SEQUENCE: 66

Lys Leu Leu Gln Asn Ser Gln Val Tyr
1               5

<210> SEQ ID NO 67
<211> LENGTH: 15
<212> TYPE: PRT
<213> ORGANISM: Artificial
<220> FEATURE:
<223> OTHER INFORMATION: Synthetic peptide

<400> SEQUENCE: 67

Ser Ala Ala Phe Glu Asp Leu Arg Val Leu Ser Phe Ile Arg Gly
1               5                   10                  15

<210> SEQ ID NO 68
<211> LENGTH: 16
<212> TYPE: PRT
<213> ORGANISM: Artificial
<220> FEATURE:
<223> OTHER INFORMATION: Synthetic peptide

<400> SEQUENCE: 68

Ser Ala Ala Phe Glu Asp Leu Arg Val Ser Ser Phe Ile Arg Gly Thr
1               5                   10                  15

<210> SEQ ID NO 69
<211> LENGTH: 16
<212> TYPE: PRT
<213> ORGANISM: Artificial
<220> FEATURE:
<223> OTHER INFORMATION: Synthetic peptide

<400> SEQUENCE: 69

Ser Ala Ala Phe Glu Asp Leu Arg Val Leu Ser Phe Ile Arg Gly Tyr
1               5                   10                  15

<210> SEQ ID NO 70
<211> LENGTH: 14
<212> TYPE: PRT
<213> ORGANISM: Artificial
<220> FEATURE:
<223> OTHER INFORMATION: Synthetic peptide

<400> SEQUENCE: 70

Glu Leu Arg Ser Arg Tyr Trp Ala Ile Arg Thr Arg Ser Gly
1               5                   10

<210> SEQ ID NO 71
<211> LENGTH: 9
<212> TYPE: PRT
<213> ORGANISM: Artificial
<220> FEATURE:
<223> OTHER INFORMATION: Synthetic peptide

<400> SEQUENCE: 71

Glu Leu Arg Ser Arg Tyr Trp Ala Ile
1               5

<210> SEQ ID NO 72
<211> LENGTH: 9
<212> TYPE: PRT
<213> ORGANISM: Artificial
<220> FEATURE:
<223> OTHER INFORMATION: Synthetic peptide

```
<400> SEQUENCE: 72

Ser Arg Tyr Trp Ala Ile Arg Thr Arg
1               5

<210> SEQ ID NO 73
<211> LENGTH: 10
<212> TYPE: PRT
<213> ORGANISM: Artificial
<220> FEATURE:
<223> OTHER INFORMATION: Synthetic peptide

<400> SEQUENCE: 73

Tyr Trp Ala Ile Arg Thr Arg Ser Gly Gly
1               5                   10

<210> SEQ ID NO 74
<211> LENGTH: 9
<212> TYPE: PRT
<213> ORGANISM: Artificial
<220> FEATURE:
<223> OTHER INFORMATION: Synthetic peptide

<400> SEQUENCE: 74

Ser Arg Tyr Trp Ala Ile Arg Thr Arg
1               5

<210> SEQ ID NO 75
<211> LENGTH: 9
<212> TYPE: PRT
<213> ORGANISM: Artificial
<220> FEATURE:
<223> OTHER INFORMATION: Synthetic peptide

<400> SEQUENCE: 75

Leu Pro Phe Asp Lys Pro Thr Ile Met
1               5

<210> SEQ ID NO 76
<211> LENGTH: 9
<212> TYPE: PRT
<213> ORGANISM: Artificial
<220> FEATURE:
<223> OTHER INFORMATION: Synthetic peptide

<400> SEQUENCE: 76

Val Ser Asp Gly Gly Pro Asn Leu Tyr
1               5

<210> SEQ ID NO 77
<211> LENGTH: 9
<212> TYPE: PRT
<213> ORGANISM: Artificial
<220> FEATURE:
<223> OTHER INFORMATION: Synthetic peptide

<400> SEQUENCE: 77

Arg Arg Ser Phe Glu Leu Lys Lys Leu
1               5

<210> SEQ ID NO 78
<211> LENGTH: 9
<212> TYPE: PRT
<213> ORGANISM: Artificial
<220> FEATURE:
<223> OTHER INFORMATION: Synthetic peptide

<400> SEQUENCE: 78
```

Arg Arg Ala Thr Ala Ile Leu Arg Lys
1               5

<210> SEQ ID NO 79
<211> LENGTH: 9
<212> TYPE: PRT
<213> ORGANISM: Artificial
<220> FEATURE:
<223> OTHER INFORMATION: Synthetic peptide

<400> SEQUENCE: 79

Arg Pro Ile Ile Arg Pro Ala Thr Leu
1               5

<210> SEQ ID NO 80
<211> LENGTH: 9
<212> TYPE: PRT
<213> ORGANISM: Artificial
<220> FEATURE:
<223> OTHER INFORMATION: Synthetic peptide

<400> SEQUENCE: 80

Ala Asp Arg Gly Leu Leu Arg Asp Ile
1               5

<210> SEQ ID NO 81
<211> LENGTH: 13
<212> TYPE: PRT
<213> ORGANISM: Artificial
<220> FEATURE:
<223> OTHER INFORMATION: Synthetic peptide

<400> SEQUENCE: 81

Pro Tyr Tyr Thr Gly Glu His Ala Lys Ala Ile Gly Asn
1               5                   10

<210> SEQ ID NO 82
<211> LENGTH: 19
<212> TYPE: PRT
<213> ORGANISM: Artificial
<220> FEATURE:
<223> OTHER INFORMATION: Synthetic peptide

<400> SEQUENCE: 82

Pro Ala Lys Leu Leu Lys Glu Arg Gly Phe Phe Gly Ala Ile Ala Gly
1               5                   10                  15

Phe Leu Glu

<210> SEQ ID NO 83
<211> LENGTH: 2199
<212> TYPE: DNA
<213> ORGANISM: Artificial
<220> FEATURE:
<223> OTHER INFORMATION: Synthetic polynucleotide

<400> SEQUENCE: 83
atgcatatga gatctccagc taaacttctg aaagaacgtg gatttttcgg tgcaatcgct      60
ggttttctgg aggggtcgaa agcctacagt aactgttacc cctacgatgt gcccgattat     120
gccagcctgg gtagcctcct tacagaagtt gaaacttatg tgctcggctg gctgacaggg     180
aaaaacggcc tttatcctgt gtggaccggc gtgacgcaga acggattctg gcgtggcgaa     240
aatggacgta aaactcgcag tgcgtatgag cgcatgtgta acatcctcaa aggtaaaggc     300
ccgaaatatg tgaaacagaa tacattaaaa ttagccaccg gcgcgagcgc tgcctttgaa     360
gacctccgtg tgctcagttt tatccgcggt tatgggggaac tgcgttctcg ctattgggcg     420

-continued

```
atccgtaccc ggtcagggggg tccaccggcg aagctgctga agaacgtgg gttcttcggt      480 gcgattgccg gtttcttgga aggatcaaaa gcgtattcga actgctaccc gtatgatgtg      540
ccagattacg ccagcctggg ctccctcttg acagaggtcg aaacctatgt actgggttgg      600
ctgaccggta agaacggtct gtatccggtt tggactggtg tgacacaaaa cggcttttgg      660 cgggggggaaa acggccggaa acccgcagc gcttacgagc gcatgtgcaa cattctgaaa      720
ggcaaaggcc cgaaatacgt gaagcagaat acgctcaaac ttgccacggg cgcaagcgca      780
gcctttgaag acctgcgggt cttgagcttt atccgcggtt acggggagct gcggtcgcgc      840
tactgggcga ttcgtacgcg tagtggtgga cctcccgcga aacttctgaa agagcggggc      900
ttctttggag cgattgcggg cttcttggag ggaagcaaag cctactctaa ttgttaccca      960
tacgatgtgc tgattatgc gagcctcggt agcttgctga cagaagtgga aacctacgtt     1020
ctcggctggc tgacgggcaa aaatggtctc tacccagtgt ggaccggagt acccagaat     1080 gggttctggc gcggtgagaa cggccgtaaa acacgttcag cgtacgagcg gatgtgcaac     1140
atcttaaaag gcaaggacc gaaatacgtc aagcagaata tctctgaagtt agccactggg     1200 gcctcagccg cctttgaaga ccttcgcgtc ttgagtttta tccggggtta tggggaactg     1260
cggagccgct actgggctat tcgtacgcgg tcgggtggcc cactcgagcc ggccaaattg     1320
ctcaaagaac gtggtttctt cggagcgatc gcaggttttc ttgaaggctc taaagcgtac     1380
agcaactgtt atccatacga tgtgccggat tacgccagtc tgggttccct cctgaccgag     1440
gtggaaacgt atgtactagg atggctcacg ggtaaaaatg gtctctatcc tgtgtggacg     1500
ggcgtaaccc agaacggctt ttggcggggc gaaaacggcc gcaaaacccg tagcgcatac     1560
gagcgtatgt gtaacatcct aaaggcaaa ggtccaaaat acgttaagca gaatacctg     1620 aaactggcta cgggcgccag tgcggccttc gaagatttac gggtgctgtc cttcatccgc     1680
ggctatggtg aactgcgctc tcgttactgg gcaatccgta cccgcagtgg cggacctccg     1740
gctaaactgt tgaaagaacg cggcttcttt ggtgctatcg caggttttct ggaaggaagt     1800
aaagcatatt cgaattgtta tccctacgac gtgccggatt atgcgtcgct cggttcgctg     1860
ctgaccgagg tggaaaccta cgttctaggc tggttgacag gtaagaacgg gctttacccg     1920
gtatggaccg gcgttaccca gaacggtttt tggcgcggtg aaaatggccg taaaactcgg     1980
tcagcatacg aacggatgtg caatatcttg aaaggtaaag gaccgaaata cgttaaacag     2040
aacacgctga aactggcaac aggcgccagc gcggcgtttg aggatttacg cgtcctgtca     2100
tttattcggg gctacggcga attacgtagt cgttattggg cgattcgtac ccgcagcgga     2160
gggctcgagt aataaaagct ttctagacat atgatgcat                            2199
```

<210> SEQ ID NO 84
<211> LENGTH: 723
<212> TYPE: PRT
<213> ORGANISM: Artificial
<220> FEATURE:
<223> OTHER INFORMATION: Synthetic polypeptide

<400> SEQUENCE: 84

```
Met His Met Arg Ser Pro Ala Lys Leu Leu Lys Glu Arg Gly Phe Phe
1               5                   10                  15

Gly Ala Ile Ala Gly Phe Leu Glu Gly Ser Lys Ala Tyr Ser Asn Cys
            20                  25                  30

Tyr Pro Tyr Asp Val Pro Asp Tyr Ala Ser Leu Gly Ser Leu Leu Thr
        35                  40                  45
```

-continued

```
Glu Val Glu Thr Tyr Val Leu Gly Trp Leu Thr Gly Lys Asn Gly Leu
     50                  55                  60

Tyr Pro Val Trp Thr Gly Val Thr Gln Asn Gly Phe Trp Arg Gly Glu
 65                  70                  75                  80

Asn Gly Arg Lys Thr Arg Ser Ala Tyr Glu Arg Met Cys Asn Ile Leu
                 85                  90                  95

Lys Gly Lys Gly Pro Lys Tyr Val Lys Gln Asn Thr Leu Lys Leu Ala
            100                 105                 110

Thr Gly Ala Ser Ala Ala Phe Glu Asp Leu Arg Val Leu Ser Phe Ile
        115                 120                 125

Arg Gly Tyr Gly Glu Leu Arg Ser Arg Tyr Trp Ala Ile Arg Thr Arg
    130                 135                 140

Ser Gly Gly Pro Pro Ala Lys Leu Leu Lys Glu Arg Gly Phe Phe Gly
145                 150                 155                 160

Ala Ile Ala Gly Phe Leu Glu Gly Ser Lys Ala Tyr Ser Asn Cys Tyr
                165                 170                 175

Pro Tyr Asp Val Pro Asp Tyr Ala Ser Leu Gly Ser Leu Leu Thr Glu
            180                 185                 190

Val Glu Thr Tyr Val Leu Gly Trp Leu Thr Gly Lys Asn Gly Leu Tyr
        195                 200                 205

Pro Val Trp Thr Gly Val Thr Gln Asn Gly Phe Trp Arg Gly Glu Asn
    210                 215                 220

Gly Arg Lys Thr Arg Ser Ala Tyr Glu Arg Met Cys Asn Ile Leu Lys
225                 230                 235                 240

Gly Lys Gly Pro Lys Tyr Val Lys Gln Asn Thr Leu Lys Leu Ala Thr
                245                 250                 255

Gly Ala Ser Ala Ala Phe Glu Asp Leu Arg Val Leu Ser Phe Ile Arg
            260                 265                 270

Gly Tyr Gly Glu Leu Arg Ser Arg Tyr Trp Ala Ile Arg Thr Arg Ser
        275                 280                 285

Gly Gly Pro Pro Ala Lys Leu Leu Lys Glu Arg Gly Phe Phe Gly Ala
    290                 295                 300

Ile Ala Gly Phe Leu Glu Gly Ser Lys Ala Tyr Ser Asn Cys Tyr Pro
305                 310                 315                 320

Tyr Asp Val Pro Asp Tyr Ala Ser Leu Gly Ser Leu Leu Thr Glu Val
                325                 330                 335

Glu Thr Tyr Val Leu Gly Trp Leu Thr Gly Lys Asn Gly Leu Tyr Pro
            340                 345                 350

Val Trp Thr Gly Val Thr Gln Asn Gly Phe Trp Arg Gly Glu Asn Gly
        355                 360                 365

Arg Lys Thr Arg Ser Ala Tyr Glu Arg Met Cys Asn Ile Leu Lys Gly
    370                 375                 380

Lys Gly Pro Lys Tyr Val Lys Gln Asn Thr Leu Lys Leu Ala Thr Gly
385                 390                 395                 400

Ala Ser Ala Ala Phe Glu Asp Leu Arg Val Leu Ser Phe Ile Arg Gly
                405                 410                 415

Tyr Gly Glu Leu Arg Ser Arg Tyr Trp Ala Ile Arg Thr Arg Ser Gly
            420                 425                 430

Gly Pro Leu Glu Pro Ala Lys Leu Leu Lys Glu Arg Gly Phe Phe Gly
        435                 440                 445

Ala Ile Ala Gly Phe Leu Glu Gly Ser Lys Ala Tyr Ser Asn Cys Tyr
    450                 455                 460

Pro Tyr Asp Val Pro Asp Tyr Ala Ser Leu Gly Ser Leu Leu Thr Glu
465                 470                 475                 480
```

Val Glu Thr Tyr Val Leu Gly Trp Leu Thr Gly Lys Asn Gly Leu Tyr
             485                 490                 495

Pro Val Trp Thr Gly Val Thr Gln Asn Gly Phe Trp Arg Gly Glu Asn
         500                 505                 510

Gly Arg Lys Thr Arg Ser Ala Tyr Glu Arg Met Cys Asn Ile Leu Lys
             515                 520                 525

Gly Lys Gly Pro Lys Tyr Val Lys Gln Asn Thr Leu Lys Leu Ala Thr
         530                 535                 540

Gly Ala Ser Ala Ala Phe Glu Asp Leu Arg Val Leu Ser Phe Ile Arg
545                 550                 555                 560

Gly Tyr Gly Glu Leu Arg Ser Arg Tyr Trp Ala Ile Arg Thr Arg Ser
                 565                 570                 575

Gly Gly Pro Pro Ala Lys Leu Leu Lys Glu Arg Gly Phe Phe Gly Ala
             580                 585                 590

Ile Ala Gly Phe Leu Glu Gly Ser Lys Ala Tyr Ser Asn Cys Tyr Pro
         595                 600                 605

Tyr Asp Val Pro Asp Tyr Ala Ser Leu Gly Ser Leu Leu Thr Glu Val
     610                 615                 620

Glu Thr Tyr Val Leu Gly Trp Leu Thr Gly Lys Asn Gly Leu Tyr Pro
625                 630                 635                 640

Val Trp Thr Gly Val Thr Gln Asn Gly Phe Trp Arg Gly Glu Asn Gly
                 645                 650                 655

Arg Lys Thr Arg Ser Ala Tyr Glu Arg Met Cys Asn Ile Leu Lys Gly
             660                 665                 670

Lys Gly Pro Lys Tyr Val Lys Gln Asn Thr Leu Lys Leu Ala Thr Gly
         675                 680                 685

Ala Ser Ala Ala Phe Glu Asp Leu Arg Val Leu Ser Phe Ile Arg Gly
     690                 695                 700

Tyr Gly Glu Leu Arg Ser Arg Tyr Trp Ala Ile Arg Thr Arg Ser Gly
705                 710                 715                 720

Gly Leu Glu

<210> SEQ ID NO 85
<211> LENGTH: 1299
<212> TYPE: DNA
<213> ORGANISM: Artificial
<220> FEATURE:
<223> OTHER INFORMATION: Synthetic polynucleotide

<400> SEQUENCE: 85
atgcatatga gatctccagc taaacttctg aaagaacgtg attttttcgg tgcaatcgct      60
ggttttctgg agccaccggc gaagctgctg aaagaacgtg ggttcttcgg tgcgattgcc     120
ggtttcttgg aacctcccgc gaaacttctg aaagagcggg gcttctttgg agcgattgcg     180
ggcttcttgg agccatcgaa agcctacagt aactgttacc cctacgatgt gcccgattat     240
gccagcctgc cttcaaaagc gtattcgaac tgctacccgt atgatgtgcc agattacgcc     300
agcctgccaa gcaaagccta ctctaattgt tacccatacg atgtgcctga ttatgcgagc     360
ctccctagcc tccttacaga agttgaaact tatgtgctca gcttgctgac agaagtggaa     420
acctacgttc tcagcttgct gacagaagtg gaaacctacg ttctctggct gacagggaaa     480
aacggccttt atccttggct gaccggtaag aacggtctgt atccgtggct gacgggcaaa     540
aatggtctct acccatggac cggcgtgacg cagaaccctt ggactggtgt gacacaaaac     600
ccatggaccg gagttaccca gaatcctttc tggcgtggcg aaaatggacg taaaactcgc     660

```
agtgcgtatg agcgcatgtg taacatcctc aaaggtaaac ccttttggcg gggggaaaac    720
ggccggaaaa cccgcagcgc ttacgagcgc atgtgcaaca ttctgaaagg caaaccattc    780
tggcgcggtg agaacggccg taaaacacgt tcagcgtacg agcggatgtg caacatctta    840
aaaggcaaac ctccgaaata cgtgaagcag aatacgctca aacttgccac gccaccgaaa    900
tacgtcaagc agaatactct gaagttagcc actccgccga atacgtcaa gcagaatact     960 ctgaagttag ccactccttc agccgccttt gaagaccttc gcgtcttgag ttttatccgg   1020
ggttatccaa gcgcagcctt tgaagacctg cgggtcttga gctttatccg cggttaccct   1080
tcagccgcct ttgaagacct tcgcgtcttg agttttatcc ggggttatcc agaactgcgt   1140
tctcgctatt gggcgatccg tacccggtca gggccggagc tgcggtcgcg ctactgggcg   1200
attcgtacgc gtagtggtcc agaactgcgg agccgctact gggctattcg tacgcggtcg   1260
ggttaataac tcgagaggct ttctagacat atgatgcat                          1299
```

<210> SEQ ID NO 86
<211> LENGTH: 421
<212> TYPE: PRT
<213> ORGANISM: Artificial
<220> FEATURE:
<223> OTHER INFORMATION: Synthetic polypeptide

<400> SEQUENCE: 86

```
Met His Met Arg Ser Pro Ala Lys Leu Leu Lys Glu Arg Gly Phe Phe
1               5                   10                  15

Gly Ala Ile Ala Gly Phe Leu Glu Pro Pro Ala Lys Leu Leu Lys Glu
            20                  25                  30

Arg Gly Phe Phe Gly Ala Ile Ala Gly Phe Leu Glu Pro Pro Ala Lys
        35                  40                  45

Leu Leu Lys Glu Arg Gly Phe Phe Gly Ala Ile Ala Gly Phe Leu Glu
    50                  55                  60

Pro Ser Lys Ala Tyr Ser Asn Cys Tyr Pro Tyr Asp Val Pro Asp Tyr
65                  70                  75                  80

Ala Ser Leu Pro Ser Lys Ala Tyr Ser Asn Cys Tyr Pro Tyr Asp Val
                85                  90                  95

Pro Asp Tyr Ala Ser Leu Pro Ser Lys Ala Tyr Ser Asn Cys Tyr Pro
            100                 105                 110

Tyr Asp Val Pro Asp Tyr Ala Ser Leu Pro Ser Leu Leu Thr Glu Val
        115                 120                 125

Glu Thr Tyr Val Leu Ser Leu Leu Thr Glu Val Glu Thr Tyr Val Leu
    130                 135                 140

Ser Leu Leu Thr Glu Val Glu Thr Tyr Val Leu Trp Leu Thr Gly Lys
145                 150                 155                 160

Asn Gly Leu Tyr Pro Trp Leu Thr Gly Lys Asn Gly Leu Tyr Pro Trp
                165                 170                 175

Leu Thr Gly Lys Asn Gly Leu Tyr Pro Trp Thr Gly Val Thr Gln Asn
            180                 185                 190

Pro Trp Thr Gly Val Thr Gln Asn Pro Trp Thr Gly Val Thr Gln Asn
        195                 200                 205

Pro Phe Trp Arg Gly Glu Asn Gly Arg Lys Thr Arg Ser Ala Tyr Glu
    210                 215                 220

Arg Met Cys Asn Ile Leu Lys Gly Lys Pro Phe Trp Arg Gly Glu Asn
225                 230                 235                 240

Gly Arg Lys Thr Arg Ser Ala Tyr Glu Arg Met Cys Asn Ile Leu Lys
                245                 250                 255
```

```
Gly Lys Pro Phe Trp Arg Gly Glu Asn Gly Arg Lys Thr Arg Ser Ala
            260                 265                 270

Tyr Glu Arg Met Cys Asn Ile Leu Lys Gly Lys Pro Pro Lys Tyr Val
        275                 280                 285

Lys Gln Asn Thr Leu Lys Leu Ala Thr Pro Pro Lys Tyr Val Lys Gln
    290                 295                 300

Asn Thr Leu Lys Leu Ala Thr Pro Pro Lys Tyr Val Lys Gln Asn Thr
305                 310                 315                 320

Leu Lys Leu Ala Thr Pro Ser Ala Ala Phe Glu Asp Leu Arg Val Leu
                325                 330                 335

Ser Phe Ile Arg Gly Tyr Pro Ser Ala Ala Phe Glu Asp Leu Arg Val
            340                 345                 350

Leu Ser Phe Ile Arg Gly Tyr Pro Ser Ala Ala Phe Glu Asp Leu Arg
        355                 360                 365

Val Leu Ser Phe Ile Arg Gly Tyr Pro Glu Leu Arg Ser Arg Tyr Trp
    370                 375                 380

Ala Ile Arg Thr Arg Ser Gly Pro Glu Leu Arg Ser Arg Tyr Trp Ala
385                 390                 395                 400

Ile Arg Thr Arg Ser Gly Pro Glu Leu Arg Ser Arg Tyr Trp Ala Ile
                405                 410                 415

Arg Thr Arg Ser Gly
            420

<210> SEQ ID NO 87
<211> LENGTH: 1335
<212> TYPE: DNA
<213> ORGANISM: Artificial
<220> FEATURE:
<223> OTHER INFORMATION: Synthetic polynucleotide

<400> SEQUENCE: 87
atgagatctc cggcgaaact gctgaaagaa cgtggctttt ttggcgcgat tgcgggcttt      60
ctggaaggca gcaaagcgta tagcaactgc tatccgtatg atgtgccgga ttacgcgagt     120
ctgggctctc tgctgaccga agtggaaacc tatgtgctgg gctggctgac cggcaaaaac     180
ggcctgtatc cggtgtggac cggcgtgacc cagaacggct tttggcgtgg cgaaaacggc     240
cgtaaaaccc gtagcgcgta tgaacgtatg tgcaacatcc tgaaaggcaa aggcccgaaa     300
tatgtgaaaa cagaacaccct gaaactggcc accggtgcga gcgcggcgtt tgaggacctg     360
cgtgttctga gctttattcg tggctatggc gaactgcgta gccgttattg gcgattcgt      420 acccgtagcg gtggtccgcc ggccaaactg ctgaaagaac gcggtttctt cggtgcgatc     480
gccggttttc tggaaggtag caaagcctac tctaattgtt acccgtacga tgttccggat     540
tacgccagcc tgggtagcct gctgaccgaa gttgaaacct acgttctggg ttggctgacc     600
ggtaaaaatg gtctgtaccc ggtttggacc ggtgttaccc agaatggttt ctggcgcggt     660
gaaaatggtc gcaaaacccg cagcgcctac gaacgcatgt gtaatattct gaaaggtaaa     720
ggtccgaaat acgttaaaca gaatacccct gaaactggcca ccggcgccag cgccgccttc     780
gaggacctgc gcgttctgag cttcatccgc ggttacggtg aactgcgcag ccgctactgg     840
gccatccgca cccgcagcgg tggtccgccg gcgaaactgc tgaaagaacg cggttttttt     900
ggtgccattc gggttttctt ggaaggtagc aaagccatt ctaactgcta tccgtacgat      960
gttccggatt atgcgagcct gggtagcctg ctgaccgaag tggaaacct atgttctggt      1020 tggctgaccg gcaaaacggg tctgtatccg gtttggaccg gtgtgaccca gaacggtttt     1080
tggcgcggtg aaaacggccg taaaacccgc agcgcctatg aacgcatgtg caacattctg    1140
```

```
aaaggcaaag gtccgaaata cgtgaaacag aacaccctga aactggccac cggcgcgagc    1200
gcggcctttg aggacctgcg cgttctgagc tttattcgcg gctatggtga actgcgcagc    1260
cgctattggg cgattcgtac ccgcagcggc ggctaataac tcgagaagct ttctagacat    1320
atgatgcatg agctc                                                    1335
```

<210> SEQ ID NO 88
<211> LENGTH: 431
<212> TYPE: PRT
<213> ORGANISM: Artificial
<220> FEATURE:
<223> OTHER INFORMATION: Synthetic polypeptide

<400> SEQUENCE: 88

```
Met Arg Ser Pro Ala Lys Leu Leu Lys Glu Arg Gly Phe Phe Gly Ala
1               5                   10                  15

Ile Ala Gly Phe Leu Glu Gly Ser Lys Ala Tyr Ser Asn Cys Tyr Pro
            20                  25                  30

Tyr Asp Val Pro Asp Tyr Ala Ser Leu Gly Ser Leu Leu Thr Glu Val
        35                  40                  45

Glu Thr Tyr Val Leu Gly Trp Leu Thr Gly Lys Asn Gly Leu Tyr Pro
50                  55                  60

Val Trp Thr Gly Val Thr Gln Asn Gly Phe Trp Arg Gly Glu Asn Gly
65                  70                  75                  80

Arg Lys Thr Arg Ser Ala Tyr Glu Arg Met Cys Asn Ile Leu Lys Gly
                85                  90                  95

Lys Gly Pro Lys Tyr Val Lys Gln Asn Thr Leu Lys Leu Ala Thr Gly
            100                 105                 110

Ala Ser Ala Ala Phe Glu Asp Leu Arg Val Leu Ser Phe Ile Arg Gly
        115                 120                 125

Tyr Gly Glu Leu Arg Ser Arg Tyr Trp Ala Ile Arg Thr Arg Ser Gly
    130                 135                 140

Gly Pro Pro Ala Lys Leu Leu Lys Glu Arg Gly Phe Phe Gly Ala Ile
145                 150                 155                 160

Ala Gly Phe Leu Glu Gly Ser Lys Ala Tyr Ser Asn Cys Tyr Pro Tyr
                165                 170                 175

Asp Val Pro Asp Tyr Ala Ser Leu Gly Ser Leu Leu Thr Glu Val Glu
            180                 185                 190

Thr Tyr Val Leu Gly Trp Leu Thr Gly Lys Asn Gly Leu Tyr Pro Val
        195                 200                 205

Trp Thr Gly Val Thr Gln Asn Gly Phe Trp Arg Gly Glu Asn Gly Arg
    210                 215                 220

Lys Thr Arg Ser Ala Tyr Glu Arg Met Cys Asn Ile Leu Lys Gly Lys
225                 230                 235                 240

Gly Pro Lys Tyr Val Lys Gln Asn Thr Leu Lys Leu Ala Thr Gly Ala
                245                 250                 255

Ser Ala Ala Phe Glu Asp Leu Arg Val Leu Ser Phe Ile Arg Gly Tyr
            260                 265                 270

Gly Glu Leu Arg Ser Arg Tyr Trp Ala Ile Arg Thr Arg Ser Gly Gly
        275                 280                 285

Pro Pro Ala Lys Leu Leu Lys Glu Arg Gly Phe Phe Gly Ala Ile Ala
    290                 295                 300

Gly Phe Leu Glu Gly Ser Lys Ala Tyr Ser Asn Cys Tyr Pro Tyr Asp
305                 310                 315                 320

Val Pro Asp Tyr Ala Ser Leu Gly Ser Leu Leu Thr Glu Val Glu Thr
```

-continued

```
                    325                 330                 335
Tyr Val Leu Gly Trp Leu Thr Gly Lys Asn Gly Leu Tyr Pro Val Trp
            340                 345                 350

Thr Gly Val Thr Gln Asn Gly Phe Trp Arg Gly Glu Asn Gly Arg Lys
        355                 360                 365

Thr Arg Ser Ala Tyr Glu Arg Met Cys Asn Ile Leu Lys Gly Lys Gly
    370                 375                 380

Pro Lys Tyr Val Lys Gln Asn Thr Leu Lys Leu Ala Thr Gly Ala Ser
385                 390                 395                 400

Ala Ala Phe Glu Asp Leu Arg Val Leu Ser Phe Ile Arg Gly Tyr Gly
            405                 410                 415

Glu Leu Arg Ser Arg Tyr Trp Ala Ile Arg Thr Arg Ser Gly Gly
            420                 425                 430
```

What is claimed is:

1. A synthetic or a recombinant influenza multi-epitope polypeptide comprising multiple copies of a plurality of influenza virus peptide epitopes wherein the polypeptide is selected from the group consisting of:
   i. $(X_1ZX_2Z\ldots X_m)_n$; and
   ii. $(X_1)_nZ(X_2)_nZ\ldots(X_m)_n$;
   wherein n is at each occurrence independently an integer of 3-6; m is 9; $X_1, X_2\ldots X_m$ are influenza peptide epitopes consisting of HA 354-372 (E1, SEQ ID NO: 82), HA 91-108 (E2, SEQ ID NO: 48), M1 2-12 (E3, SEQ ID NO: 25), HA 150-159 (E4, SEQ ID NO: 52), HA 143-149 (E5, SEQ ID NO: 51), NP 206-229 (E6, SEQ ID NO: 64), HA 307-319 (E7, SEQ ID NO: 59), NP 335-350 (E8, SEQ ID NO: 69), and NP 380-393 (E9, SEQ ID NO: 70); Z at each occurrence is a bond or a spacer of 1 to 4 neutral amino acid residues.

2. The polypeptide according to claim 1, comprising three repeats of nine different influenza virus peptide epitopes arranged in the following block copolymer structure:
   [E1E1E1-E2E2E2-E3E3E3-E4E4E4-E5E5E5-E6E6E6-E7E7E7-E8E8E8-E9E9E9].

3. The polypeptide according to claim 2 as set forth in a sequence selected from the group consisting of SEQ ID NO:84, SEQ ID NO:86 and SEQ ID NO:88.

4. The polypeptide according to claim 1 further comprising a carrier sequence.

5. The polypeptide according to claim 4, wherein the peptide epitopes are inserted within the sequence of a carrier polypeptide.

6. A vaccine for immunization of a subject against influenza comprising at least one polypeptide according to claim 1.

7. The vaccine according to claim 6 wherein the polypeptide comprises three repeats of nine different influenza virus peptide epitopes arranged in the following block copolymer structure:
   [E1E1E1-E2E2E2-E3E3E3-E4E4E4-E5E5E5-E6E6E6-E7E7E7-E8E8E8-E9E9E9].

8. The vaccine according to claim 6 further comprising an adjuvant.

9. The vaccine according to claim 8 wherein the adjuvant is selected from the group consisting of: water in oil emulsion, lipid emulsion, and liposomes.

10. A polypeptide comprising a sequence selected from the group consisting of:

nine different influenza virus peptide epitopes arranged in the following alternating sequential polymeric structure [E1E2E3E4E5E6E7E8E9]$_n$, wherein n is 3 or 5;

three repeats of nine different influenza virus peptide epitopes arranged in the following block copolymer structure [E1E1E1-E2E2E2-E3E3E3-E4E4E4-E5E5E5-E6E6E6-E7E7E7-E8E8E8-E9E9E9];

six repeats of five different B-cell type influenza virus peptide epitopes arranged in the following alternating sequential polymeric structure [E1E2E3E4E5]$_6$;

six repeats of four different T-cell type influenza virus peptide epitopes arranged in the following alternating sequential polymeric structure [E7E8E9E6]$_6$;

four repeats of four different T-cell type influenza virus peptide epitopes arranged in the following alternating sequential polymeric structure [E7E8E9E6]$_4$; and six repeats of nine different influenza virus peptide epitopes arranged in the following block copolymer structure [E2E2E2E2E2E2-E1E1E1E1E1E1-E3E3E3E3E3E3-E4E4E4E4E4E4-E5E5E5E5E5E5-E6E6E6E6E6E66-E7E7E7E7E7E7-E8E8E8E8E8E8-E9E9E9E9E9E9];

wherein E1 is HA 354-372(SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

11. A polypeptide comprising a sequence of four to six repeats of:
   the four different T-cell influenza virus peptide epitopes E6, E7, E8, and E9; or
   the five different B-cell influenza virus peptide epitopes E1, E2, E3, E4, and E5;
   wherein E1 is HA 354-372(SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59), E8 is NP 335-350 (SEQ ID NO:69), and E9 is NP 380-393 (SEQ ID NO:70).

12. The polypeptide of claim 11, wherein the four peptide epitopes are arranged in one of the alternating sequence of E7E8E9E6 or the five peptide epitopes are arranged in the following alternating sequence of E1E2E3E4E5.

13. A vaccine for immunization of a subject against influenza comprising at least one polypeptide according to claim 11.

\* \* \* \* \*